United States Patent
Huisman et al.

(10) Patent No.: US 10,273,229 B2
(45) Date of Patent: Apr. 30, 2019

(54) N-SUBSTITUTED 4-AMINOQUINAZOLINE DERIVATIVES AND METHODS OF USE

(71) Applicant: Codexis, Inc., Redwood City, CA (US)

(72) Inventors: Gjalt W. Huisman, Redwood City, CA (US); Jed Lee Hubbs, Thalwil (CH); Xiyun Zhang, Fremont, CA (US); Robert Osborne, Raleigh, NC (US)

(73) Assignee: Codexis, Inc., Redwood City, CA (US)

( * ) Notice: Subject to any disclaimer, the term of this patent is extended or adjusted under 35 U.S.C. 154(b) by 22 days.

(21) Appl. No.: 15/504,120

(22) PCT Filed: Aug. 27, 2015

(86) PCT No.: PCT/US2015/047133
§ 371 (c)(1),
(2) Date: Feb. 15, 2017

(87) PCT Pub. No.: WO2016/033296
PCT Pub. Date: Mar. 3, 2016

(65) Prior Publication Data
US 2017/0334886 A1 Nov. 23, 2017

Related U.S. Application Data

(60) Provisional application No. 62/043,265, filed on Aug. 28, 2014.

(51) Int. Cl.
| | | |
|---|---|---|
| *C07D 405/04* | (2006.01) | |
| *C12Q 1/48* | (2006.01) | |
| *C07D 405/14* | (2006.01) | |
| *C12P 17/16* | (2006.01) | |
| *A61K 31/517* | (2006.01) | |
| *C07D 487/04* | (2006.01) | |
| *C07D 487/08* | (2006.01) | |

(52) U.S. Cl.
CPC .......... *C07D 405/04* (2013.01); *A61K 31/517* (2013.01); *C07D 405/14* (2013.01); *C07D 487/04* (2013.01); *C07D 487/08* (2013.01); *C12P 17/165* (2013.01); *C12Q 1/485* (2013.01); *C12Y 114/00* (2013.01); *C12Y 207/00* (2013.01); *G01N 2333/91205* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | |
|---|---|---|
| 6,117,679 A | 9/2000 | Stemmer |
| 6,376,246 B1 | 4/2002 | Crameri et al. |
| 6,586,182 B1 | 7/2003 | Patten et al. |
| 7,265,123 B2 | 9/2007 | Cockerill et al. |
| 8,252,805 B2 | 8/2012 | Metsger et al. |
| 8,543,262 B1 | 9/2013 | Gehrke et al. |
| 2005/0143401 A1 | 6/2005 | Cockerill et al. |
| 2008/0220990 A1 | 9/2008 | Fox |
| 2009/0312196 A1 | 12/2009 | Colbeck et al. |
| 2011/0053964 A1 | 3/2011 | Tung et al. |
| 2011/0300132 A1 | 12/2011 | Tung et al. |

OTHER PUBLICATIONS

Hardy, Klarissa D; et al; "Studies on the Role of Metabolic Activation in Tyrosine Kinase Inhibitor-Dependent Hepatotoxicity: Induction of CYP3A4 Enhances the Cytotoxicity of Lapatinib in HepaRG Cells" Drug Metabolism and Disposition, 42, 162-171, 2014 (Year: 2014).*

Barbara, J.E., et al., "Metabolism-Dependent Inhibition of CYP3A4 by Lapatinib: Evidence for Formation of a Metabolic Intermediate Complex with a Nitroso/Oxime Metabolite Formed via a Nitrone Intermediate," Drug Metabolism and Disposition, 41(5):1012-1022 [2013].

Hardy, K.D., et al., "Studies on the Role of Metabolic Activation in Tyrosine Kinase Inhibitor-Dependent Hepatotoxicity: Induction of CYP3A4 Enhances the Cytotoxicity of Lapatinib in HepaRG Cells," Drug Metabolism and Disposition, 42(1):162-171 [2014].

Paul, M.K., et al., "Tyrosine kinase—Role and significance in Cancer," Int. J. Med. Sci., 1(2):101-115 [2004].

Paul, S.M., et al., "How to improve R&D productivity: the pharmaceutical industry's grand challenge," Nat. Rev. Drug Disc., 9:203-214 [2010].

* cited by examiner

Primary Examiner — David W Berke-Schlessel
(74) Attorney, Agent, or Firm — Codexis, Inc.

(57) ABSTRACT

The present invention provides kinase inhibitor analogs with improved properties, such as improved efficacy, pharmacokinetics, safety, and specificity. In some embodiments, the present invention provides lapatinib analogs that provide therapeutic benefits.

5 Claims, 2 Drawing Sheets

N-SUBSTITUTED 4-AMINOQUINAZOLINE DERIVATIVES AND METHODS OF USE

The present application is a national stage application filed under 35 USC § 371 and claims priority to PCT International Application No. PCT/US2015/047133, filed Aug. 27, 2015, which claims priority to previously filed US Provisional Application. Ser. No. 62/043,265, filed Aug. 28, 2014, both of which are hereby incorporated by reference, in their entireties and for all purposes.

FIELD OF THE INVENTION

The present invention provides kinase inhibitor analogs with improved properties, such as improved efficacy, pharmacokinetics, safety, and specificity. In some embodiments, the present invention provides lapatinib analogs that provide therapeutic benefits.

BACKGROUND

Lapatinib (N-[3-chloro-4-[(3-fluorophenyl)methyoxy]phenyl]-6-[5-[2-methylsulfonylethyl-amino)methyl]-2-furyl] quinazolin-4-amine) is used in the form of lapatinib ditosylate as an oral drug to treat breast cancer and other solid tumors. It reversibly blocks phosphorylation of the epidermal growth factor receptor (EGFR), ErbB2, Erk-1 Erk-2 kinases, and AKT kinases. It also inhibits cyclin D protein levels in tumor cell lines and xenografts. It acts as a dual tyrosine kinase inhibitor that interrupts the HER2/neu and EGFR pathways, resulting in a decrease in tumor-causing cancer stem cells. It is typically used in combination therapy (e.g., with capecitabine) to treat patients with certain types of advanced breast cancer. Although it is apparently fairly well tolerated by patients, with the most common side effects being diarrhea, fatigue, nausea, and rashes, it has been associated with liver damage that can be severe or life-threatening. QT-prolongation has also been reported. Lapatinib is used with caution in patients with hypokalemia, hypomagnesmia, congenital long QT syndrome, or with co-administration of medications known to cause QT-prolongation. There have been reports of reversible decreased left ventricular function when used in combination with capecitabine (See, NCI Cancer Drug Information, FDA Approval for Lapatinib Ditosylate [Tykerb®]). Thus, there is a need for similarly or more effective drugs with an improved safety profile.

SUMMARY OF THE INVENTION

The present invention provides kinase inhibitor analogs with improved properties, such as improved efficacy, pharmacokinetics, safety, and specificity. In some embodiments, the present invention provides lapatinib analogs that provide therapeutic benefits.

The present invention provides compounds comprising formula I:

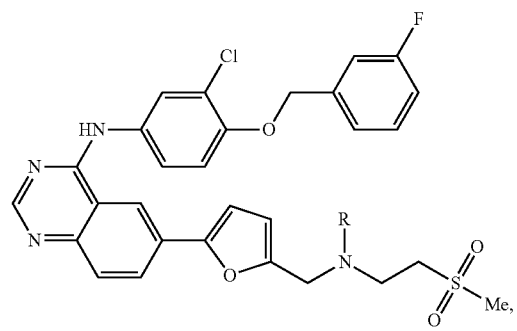

wherein R is optionally substituted cycloalkyl, cycloalkylalkyl, aryl, arylalkyl, heteroaryl, heteroarylalkyl, heteroalkyl, heteroalkylaryl, alkoxy, aryloxy, carboxyalkyl, carbonyloxy, substituted carbonyl, acetic acid, acetic acid ester, fatty acid, fatty acid ester, amino, substituted amino, aminoalkyl, haloalkyl, hydroxyalkyl, or sulfonyl. In some embodiments, R is optionally substituted cycloalkyl, heteroalkyl, alkoxy, carboxyalkyl, carbonyloxy, substituted carbonyl, acetic acid, acetic acid ester, or sulfonyl. In some additional embodiments, R is cycloalkyl, heteroalkyl, alkoxy, carboxyalkyl, carbonyloxy, substituted carbonyl, acetic acid, acetic acid ester, or sulfonyl. In some additional embodiments, the compounds comprise one of the following structures:

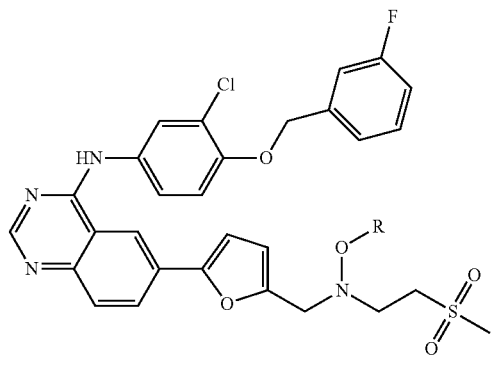

R = H, Me, Et, i-Pr

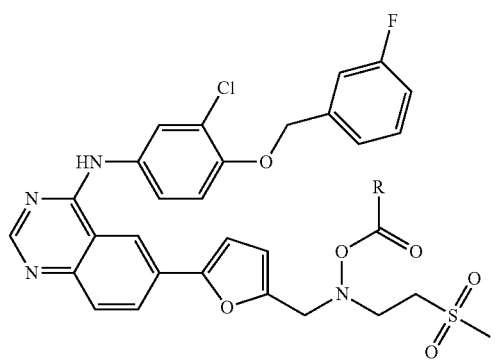

R = H, Me, Et, i-Pr, c-Pr, c-Bu, Ph, 4-F—Ph, 2-imidazxolyl

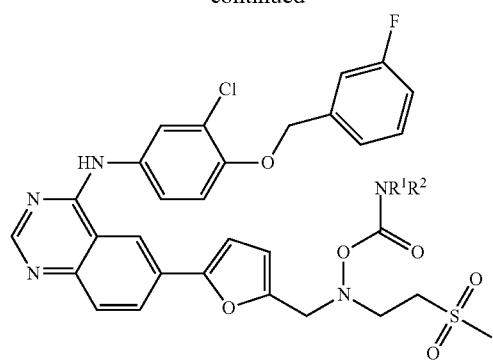
R¹R² = H, Me; H, F₃CCH₂; Me, Me;
(CH₂)₃, (CH₂)₄
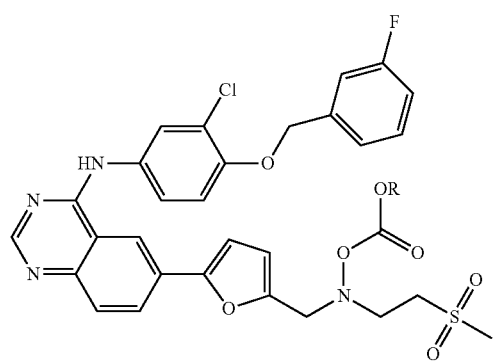
R = Me, Et, i-Pr, c-Pr, c-Bu
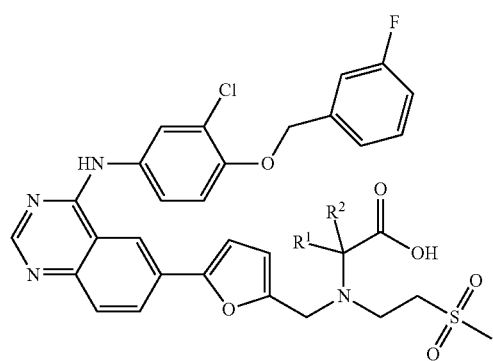
R¹R² = H, Me; H, i-Pr; H, c-Pr, c-Bu; Me, Me;
(CH₂)₃; (CH₂)₄; (CH₂OCH₂); H, CF₃
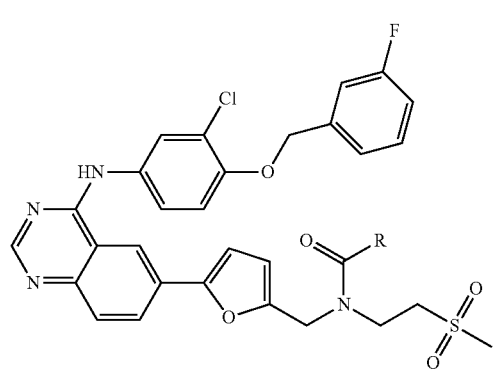
R = H, Me, Et, i-Pr, c-Pr, c-Bu, Ph,
4-F—Ph, 2-imidazolyl
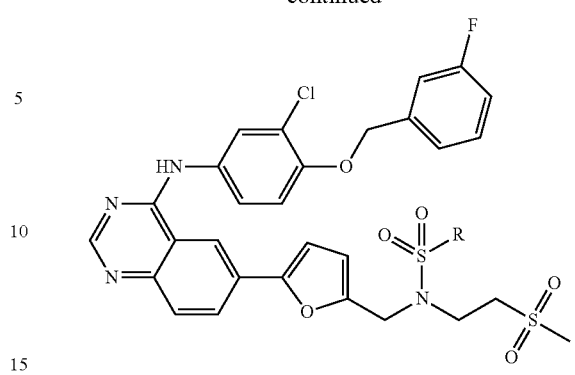
R = H, Me, Et, i-Pr, c-Pr, c-Bu, Ph,
4-F—Ph, 2-imidazolyl
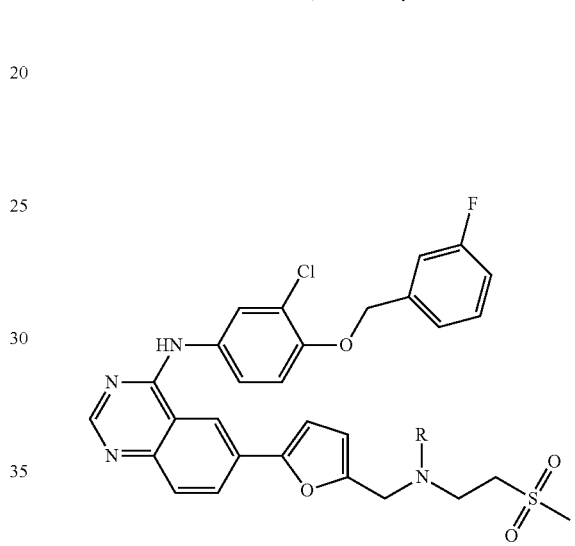
R =
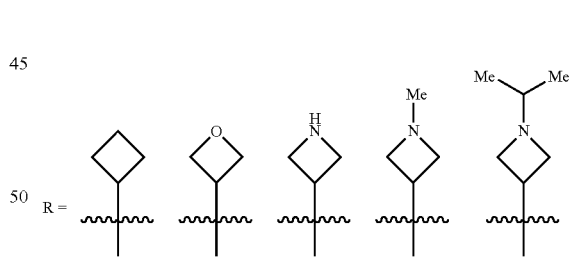
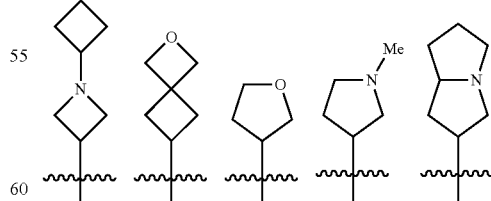
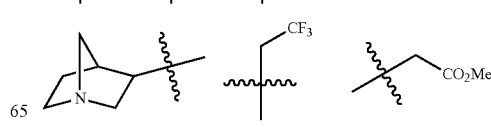

In some additional embodiments, the compound comprises one of the following structures:

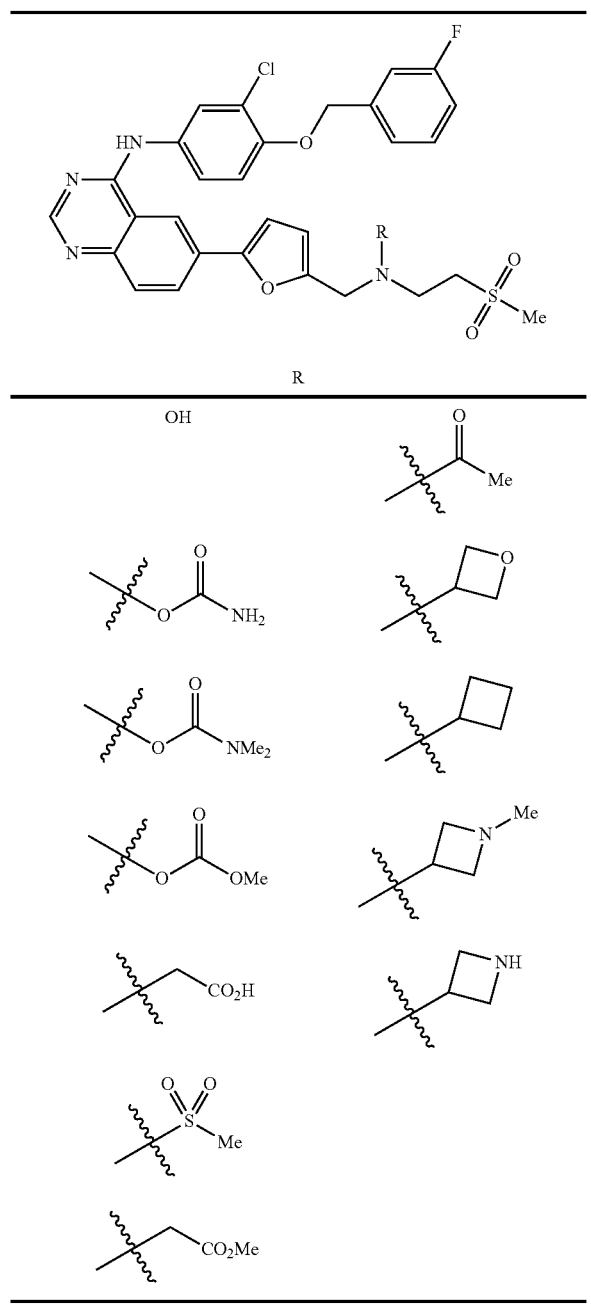

The present invention also provides compositions comprising the compounds provided herein (i.e., compounds 2 through 10) in various compositions (e.g., pharmaceutical compositions/formulations). In some embodiments, these compositions find use in treating disease. In some additional embodiments, these compounds and/or compositions are administered to an animal. In some embodiments, the compositions and/or compounds are administered to humans. However, it is not intended that the present invention be limited to the use of the present compounds and/or compositions comprising them in the field of human medical treatment, as it is contemplated that the compounds and/or compositions comprising them will find use in other suitable fields.

The present invention also provides methods for producing an improved kinase inhibitor analog comprising exposing a starting kinase inhibitor to a cytochrome P450 monooxygenase to produce an analog, purifying said analog, and determining the kinase inhibition activity of said analog. In some embodiments, the kinase inhibitor analog comprises an introduced hydroxyl moiety. In some additional embodiments, the kinase inhibitor is further modified to provide additional kinase inhibitors. In still some further embodiments, the site of hydroxylation is further modified chemically to provide new kinase inhibitors. In some additional embodiments, the starting kinase inhibitor is lapatinib.

DESCRIPTION OF THE INVENTION

Figure 1:
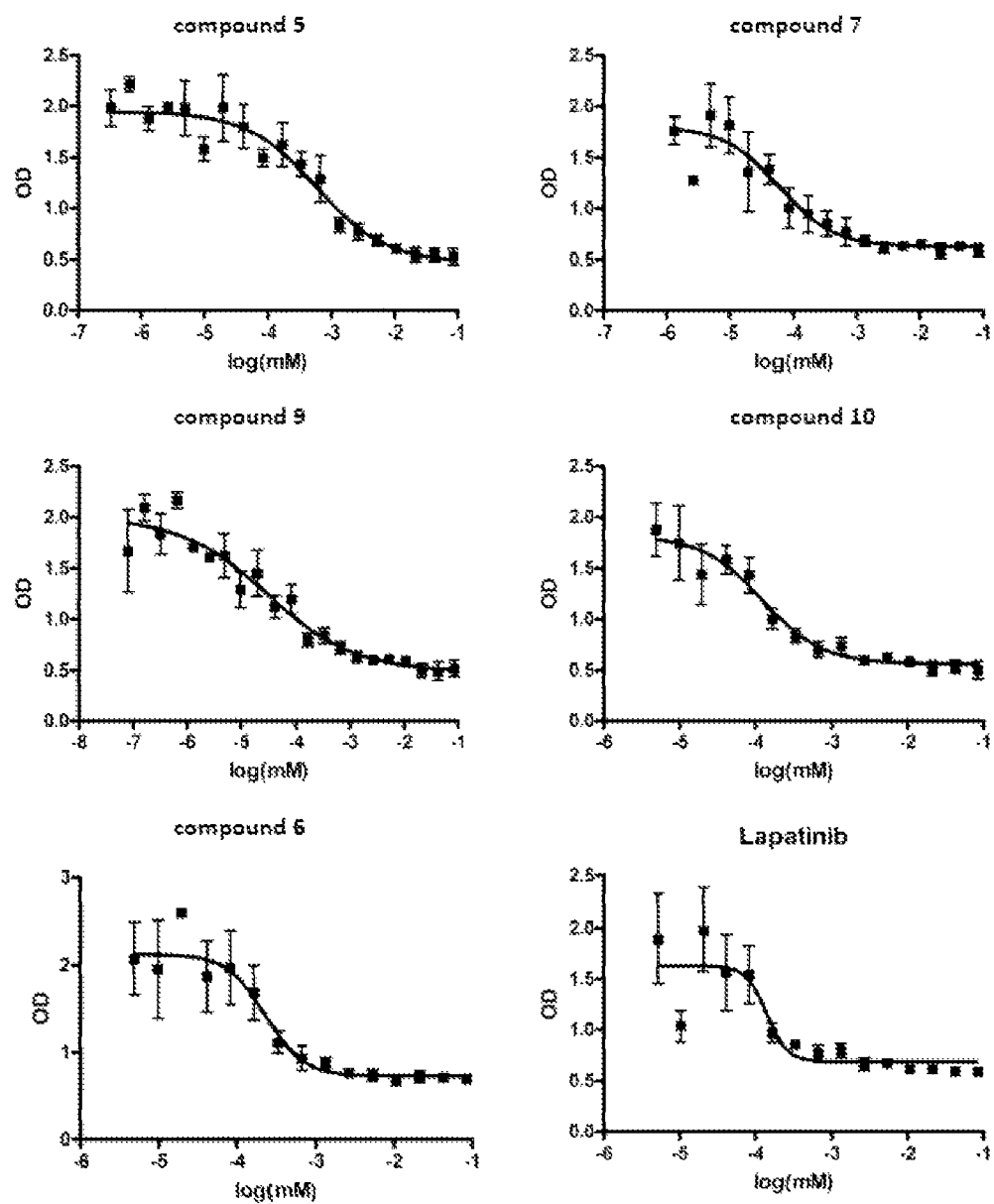
FIG. 1 provides graphs showing the cytotoxicity of various compounds tested in assays with BT-474 cells.

The present invention provides kinase inhibitor analogs with improved properties, such as improved efficacy, pharmacokinetics, safety, and specificity. In some embodiments, the present invention provides lapatinib analogs that provide therapeutic benefits.

All patents and publications, including all sequences disclosed within such patents and publications, referred to herein are expressly incorporated by reference. Unless otherwise indicated, the practice of the present invention involves conventional techniques commonly used in synthetic chemistry, medicinal chemistry, pharmacology, molecular biology, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, some methods and materials are described herein. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

Definitions

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, a small molecule etc.) or other component that is removed from at least one other component with which it is associated.

As used herein, the term "wild-type" refers to naturally-occurring organisms, enzymes and/or other proteins (e.g., non-recombinant proteins).

As used herein, "lapatinib" refers to the molecule (N-[3-chloro-4-[(3-fluorophenyl)methyoxy]phenyl]-6-[5-[2-methylsulfonylethylamino)methyl]-2-furyl] quinazolin-4-amine), either alone or in combination with other molecules (e.g., adjuvants, etc.). It is intended that the term encompass any form of the molecule, including, but not limited to lapatinib ditosylate (i.e., the ditosylate salt of lapatinib).

As used herein, "analog" refers to a compound that resembles another compound with respect to structure and/or function. The present invention provides lapatinib analogs with improved properties, as compared to lapatinib.

The terms "improved" or "improved properties," as used in the context of describing the properties of a lapatinib analog that exhibits an improvement in a property or properties as compared to another lapatinib analogs and/or a specified reference compound. Improved properties include, but are not limited to such properties as improved pharmacokinetics (e.g., lower clearance, longer half life, favorable distribution, improved bioavailability, etc.), reduced safety liabilities (e.g., reduced interaction with undesirable targets, such as hERG, liver CYPS, etc.), differential kinase specificity, and any other relevant properties taken into consideration during drug development.

As used herein, the term "tyrosine kinase" refers to protein kinase enzymes that are involved in various cell functions, including cell signaling, growth, and division through phosphorylation of proteins by the transfer of phosphate groups from ATP to proteins. Tyrosine phosphorylation by tyrosine kinases modulates enzymatic activity and creates binding sites used in recruitment of downstream signaling proteins. Tyrosine kinases are classified as receptor tyrosine kinases (RTK; e.g., EGFR, PDGFR, and FGFR, etc.) and non-receptor tyrosine kinases (NRTK; e.g., SRC, ABL, FAK, etc.) (See e.g., Paul and Mukhopadhyay, Int. J. Med. Sci., 1:101-115 [2004]). In addition to being kinases, the RTKs are cell surface transmembrane receptors. NRTKs are cytoplasmic proteins with a kinase domain and other signaling or protein-protein interacting domains. Tyrosine kinases either directly or indirectly participate in the signal transduction pathways of a variety of cellular activities, including proliferation, adhesion and migration and differentiation. As tyrosine kinases are critical components in cell signaling pathways, their activity is highly regulated in normal cells. However, if the enzyme is mutated or otherwise impacted, malignancy can occur (e.g., "oncogenic tyrosine kinase"). Diseases associated with tyrosine kinase activity include proliferation of tumor cells, pathological neovascularisation that promotes the growth of solid tumors, ocular neovascularisation (diabetic retinopathy, age-induced macular degeneration and the like) and inflammation (psoriasis, rheumatoid arthritis and the like).

As used herein, the term "kinase inhibitor" and "inhibitor of kinase activity" refer to compounds that interact with at least one kinase and inhibit the enzymatic activity of the kinase(s).

As used herein, the term "inhibiting kinase activity" refers to reducing the ability of a kinase to transfer a phosphate group from a donor molecule (e.g., ATP) to a specific target molecule (i.e., a substrate). In some embodiments, the inhibition of kinase activity is at least about 10%, as compared to an uninhibited kinase. In some other embodiments, the reduction in kinase activity is at least about 25%, at least about 50%, at least about 75%, at least about 90%, at least about 95%, at least about 99%, or 100%, as compared to uninhibited kinase.

As used herein, the "$IC_{50}$ value" refers to the concentration of kinase inhibitor that reduces the activity of a kinase to 50% of that of an uninhibited enzyme.

As used herein, the term "inhibiting effective amount" refers to a dosage sufficient to cause kinase activity inhibition.

In some embodiments, the inhibition is "specific," that the kinase inhibitor reduces the ability of a kinase to transfer a phosphate group from a donor molecule (e.g., ATP) to a specific target molecule (e.g., a substrate, such as tyrosine) at a concentration that is lower than the concentration of the inhibitor that is required to produce another, unrelated biological effect. In some embodiments, the concentration of inhibitor required for kinase inhibitory activity is at least 2-fold lower, at least 5-fold lower, at least 10-fold lower, at least 20-fold lower, or at least 25-fold lower than the concentration of the inhibitor to produce an unrelated biological effect.

As used herein, the terms "tyrosine kinase inhibitor," "tyrphostin," "tyrosine phosphorylation inhibitor," and "TKI" refer to drugs that inhibit tyrosine kinases. These TKIs are often effective in treating malignancies. In general, they compete with the ATP binding site of the catalytic domain of oncogenic tyrosine kinases. These inhibitors interfere with specific cell signaling pathways and provide target-specific therapy for certain malignancies.

As used herein, the term "tyrosine kinase-induced diseases or conditions" refers to pathological conditions that depend upon the activity of at least one tyrosine kinase.

As used herein, the term "medicament" refers any substance suitable for medical and/or veterinary use in treating any disease or condition.

As used herein, the term "pharmaceutical formulation" refers to compositions (i.e., medicaments) in any formulation suitable for administration to humans and/or other animals. As used herein, the pharmaceutical formulations of the present invention comprise at least one lapatinib analog provided herein. It is not intended that the present invention be limited to any particular type of formulation, as liquid, solid, emulsions and any other suitable formulations find use in the present invention. It is intended that any suitable means of administration of the pharmaceutical formulations find use in the present invention, including but not limited to intravenous, subcutaneous, oral, rectal, etc. It is also intended that the formulations are in any suitable format (e.g., tablets, capsules, suppositories, liquids, gels, emulsions, etc.).

As used herein, the term "pharmaceutically acceptable salt" in the present invention refers to an active ingredient which comprises at least one lapatinib analog provided herein in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of the active ingredient, with respect to its therapeutic efficacy in vivo.

The present invention furthermore provides medicaments comprising at least one lapatinib analog of the present invention and/or pharmaceutically useful salts and stereoisomers thereof, including mixtures in all ratios, and optionally excipients and/or adjuvants.

As used herein, the terms "administration" and "administering" refer to the introduction of a composition (e.g., a pharmaceutical formulation) into or on the body of a human or other animal.

As used herein, the term "therapeutically effective" refers to the ability of a pharmaceutical formulation to effectively treat the disease and/or condition for which it is administered to a human or other animal.

As used herein the term "therapeutically effective amount" refers to the amount and/or concentration of a composition (e.g., pharmaceutical formulation), that when administered to a patient, elicits the desired therapeutic effect. In some embodiments, the therapeutic effect is dependent upon the disease being treated and the desired results, as well as the individual patient (e.g., weight, stage of disease, physical and/or psychological condition, etc.).

As used herein, the terms "treating cancer" and "treatment of cancer" refer to administration of at least one composition to a mammal afflicted with a cancerous condition under conditions such that the cancerous condition is reduced or eliminated.

As used herein, "conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a polypeptide can be expressed as "percent conversion" of the substrate to the product.

As used herein, "suitable reaction conditions" refer to those conditions in the biocatalytic reaction solution (e.g., ranges of enzyme loading, substrate loading, cofactor loading, temperature, pH, buffers, co-solvents, etc.) under which a compound of the present invention is capable of converting a substrate compound to a product compound. Exemplary "suitable reaction conditions" are provided in the present disclosure and illustrated by the Examples.

As used herein, "loading", such as in "compound loading" or "enzyme loading" or "cofactor loading" refers to the concentration or amount of a component in a reaction mixture at the start of the reaction.

As used herein, "substrate," used in the context of a biocatalyst mediated process refers to the compound or molecule acted on by the biocatalyst.

As used herein, "product" used in the context of a biocatalyst mediated process refers to the compound or molecule resulting from the action of the biocatalyst.

As used herein, the term "Cyp" refers to cytochrome P450 monooxygenase. In some embodiments, the present invention comprises the use of cytochrome P450 monooxygenase variants (i.e., recombinant cytochrome P450 monooxygenase enzymes).

As used herein, "alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis, e.g., ($C_1$-$C_6$) alkyl refers to an alkyl of 1 to 6 carbon atoms.

As used herein, "alkenyl" refers to groups of from 2 to 12 carbon atoms inclusively, either straight or branched containing at least one double bond but optionally containing more than one double bond.

As used herein, "alkynyl" refers to groups of from 2 to 12 carbon atoms inclusively, either straight or branched containing at least one triple bond but optionally containing more than one triple bond, and additionally optionally containing one or more double bonded moieties.

As used herein, "cycloalkyl" refers to cyclic alkyl groups of from 3 to 12 carbon atoms inclusively having a single cyclic ring or multiple condensed rings which can be optionally substituted with from 1 to 3 alkyl groups. Exemplary cycloalkyl groups include, but are not limited to, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

As used herein, "cycloalkylalkyl" refers to an alkyl substituted with a cycloalkyl, i.e., cycloalkyl-alkyl- groups, preferably having from 1 to 6 carbon atoms inclusively in the alkyl moiety and from 3 to 12 carbon atoms inclusively in the cycloalkyl moiety. Such cycloalkylalkyl groups are exemplified by cyclopropylmethyl, cyclohexylethyl and the like.

As used herein, "aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, naphthyl, and the like.

As used herein, "arylalkyl" refers to an alkyl substituted with an aryl, i.e., aryl-alkyl- groups, preferably having from 1 to 6 carbon atoms inclusively in the alkyl moiety and from 6 to 12 carbon atoms inclusively in the aryl moiety. Such arylalkyl groups are exemplified by benzyl, phenethyl and the like.

As used herein, "heteroalkyl, "heteroalkenyl," and "heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —$NR^y$—, —PH—, —S(O)—, —$S(O)_2$—, —$S(O)NR^y$—, —$S(O)_2NR^y$—, and the like, including combinations thereof, where each $R^y$ is independently selected from hydrogen, alkyl, heteroalkyl, cycloalkyl, heterocycloalkyl, aryl, and heteroaryl.

As used herein, "heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

As used herein, "heteroarylalkyl" refers to an alkyl substituted with a heteroaryl, i.e., heteroaryl-alkyl- groups, preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

As used herein, "heterocycle," "heterocyclic," and interchangeably "heterocycloalkyl" refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

As used herein, "heterocycloalkylalkyl" refers to an alkyl substituted with a heterocycloalkyl (i.e., heterocycloalkyl-alkyl- groups), preferably having from 1 to 6 carbon atoms inclusively in the alkyl moiety and from 3 to 12 ring atoms inclusively in the heterocycloalkyl moiety.

As used herein, "oxy" refers to a divalent group —O—, which may have various substituents to form different oxy groups, including ethers and esters.

As used herein, "alkoxy" or "alkyloxy" are used interchangeably herein to refer to the group —OR$^\xi$, wherein R$^\xi$ is an alkyl group, including optionally substituted alkyl groups.

As used herein, "aryloxy" as used herein refer to the group —OR wherein R is an aryl group as defined above including optionally substituted aryl groups as also defined herein.

As used herein, "carbonyloxy" refers to the group —O(CO)R wherein R is selected from hydrogen or optionally substituted alkyl, cycloalkyl, cycloheteroalkyl, alkoxy, carboxy, aryl, aryloxy, amino, substituted amino, heteroaryl, heteroalkyl, heteroalkylalkyl, heteroarylalkyl, and the like.

As used herein, "carboxy" refers to —COOH.

As used herein, "carboxyalkyl" refers to an alkyl substituted with a carboxy group.

As used herein, "carbonyl" refers to the group —C(O)—. Substituted carbonyl refers to the group R$^\eta$—C(O)—R$^\eta$, where each R$^\eta$ is independently selected from optionally substituted alkyl, cycloalkyl, cycloheteroalkyl, alkoxy, carboxy, aryl, aryloxy, heteroaryl, heteroarylalkyl, acyl, alkoxycarbonyl, sulfanyl, sulfinyl, sulfonyl, and the like. Typical substituted carbonyl groups including acids, ketones, aldehydes, amides, esters, acyl halides, thioesters, and the like.

As used herein, "amino" refers to the group —NH$_2$. Substituted amino refers to the group —NHR$^\eta$, NR$^\eta$R$^\eta$, and NR$^\eta$R$^\eta$R$^\eta$, where each R$^\eta$ is independently selected from optionally substituted alkyl, cycloalkyl, cycloheteroalkyl, alkoxy, carboxy, aryl, aryloxy, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylsulfonylamino, furanyl-oxy-sulfamino, and the like.

A substituted amino group —NR$^\eta$R$^\eta$, can also comprise a heterocycle with attachment at nitrogen, examples include azetidine, morpholine, etc. This heterocycle can also form part of a spirocyclic, bridged- or fused-bicyclic system.

As used herein, "aminoalkyl" refers to an alkyl group in which one or more of the hydrogen atoms are replaced with an amino group, including a substituted amino group.

As used herein, "aminocarbonyl" refers to a carbonyl group substituted with an amino group, including a substituted amino group, as defined herein, and includes amides.

As used herein, "aminocarbonylalkyl" refers to an alkyl substituted with an aminocarbonyl group, as defined herein.

As used herein, "halogen" and "halo" refer to fluoro, chloro, bromo and iodo.

As used herein, "haloalkyl" refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "($C_1$ $C_2$) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

As used herein, "hydroxy" refers to —OH.

As used herein, "hydroxyalkyl" refers to an alkyl substituted with one or more hydroxy group.

As used herein, "thio" and "sulfanyl" refer to —SH. Substituted thio or sulfanyl refers to —S—R$^\eta$, where R$^\eta$ is an alkyl, aryl or other suitable substituent.

As used herein, "alkylthio" refers to —SR$^\xi$, where R$^\xi$ is an alkyl, which can be optionally substituted. Typical alkylthio group include, but are not limited to, methylthio, ethylthio, n-propylthio, and the like.

As used herein, "alkylthioalkyl" refers to an alkyl substituted with an alkylthio group, —SR$^\xi$, where R$^\xi$ is an alkyl, which can be optionally substituted.

As used herein, "sulfonyl" refers to —SO$_2$—. Substituted sulfonyl refers to -SO$_2$—R$^\eta$, where R$^\eta$ is an alkyl, aryl or other suitable substituent.

As used herein, "alkylsulfonyl" refers to —SO$_2$—R$^\xi$, where R$^\xi$ is an alkyl, which can be optionally substituted. Typical alkylsulfonyl groups include, but are not limited to, methylsulfonyl, ethylsulfonyl, n-propylsulfonyl, and the like.

As used herein, "alkylsulfonylalkyl" refers to an alkyl substituted with an alkylsulfonyl group, SO$_2$—R$^\xi$, where R$^\xi$ is an alkyl, which can be optionally substituted.

As used herein, "membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

As used herein, "fused bicyclic ring" refers to both unsubstituted and substituted carbocyclic and/or heterocyclic ring moieties having 5 or 8 atoms in each ring, the rings having 2 common atoms.

As used herein, "optionally substituted" as used herein with respect to the foregoing chemical groups means that positions of the chemical group occupied by hydrogen can be substituted with another atom, such as carbon, oxygen, nitrogen, or sulfur, or a chemical group, exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; where preferred heteroatoms are oxygen, nitrogen, and sulfur. Additionally, where open valences exist on these substitute chemical groups they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further contemplated that the above substitutions can be made provided that replacing the hydrogen with the substituent does not introduce unacceptable instability to the molecules of the present disclosure, and is otherwise chemically reasonable. One of ordinary skill in the art would understand that with respect to any chemical group described as optionally substituted, only sterically practical and/or synthetically feasible chemical groups are meant to be included. Finally, "optionally substituted" as used herein refers to all subsequent modifiers in a term or series of chemical groups. For example, in the term "optionally substituted arylalkyl," the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention.

As used herein, "recombinant" used in reference to a cell or vector, refers to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. Thus, "recombinant" or "engineered" or "non-naturally occurring" when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level. "Recombination," "recombining" and generating a "recombined" nucleic acid generally encompass the assembly of at least two nucleic acid fragments. In some embodiments, "Recombination," "recombining," and generating a "recombined" nucleic acid also encompass the assembly of two or more nucleic acid fragments wherein the assembly gives rise to a chimeric gene.

DESCRIPTION OF THE INVENTION

Compounds of the present invention include analogs of pharmaceutically active molecules that are generated via hydroxylation of the pharmaceutically active molecule, followed by further chemical or biocatalytic modification of such hydroxylated pharmaceutically active molecules. In some embodiments, the pharmaceutically active molecules are tyrosine kinase inhibitors, and the compounds of the invention are substituted derivatives of hydroxylated analogs of tyrosine kinase inhibitors.

In some embodiments, the present invention provides a compound of formula I wherein a hydrogen atom is replaced by a hydroxyl group (—OH) to give a compound that is chemically stable (i.e., does not spontaneously degrade).

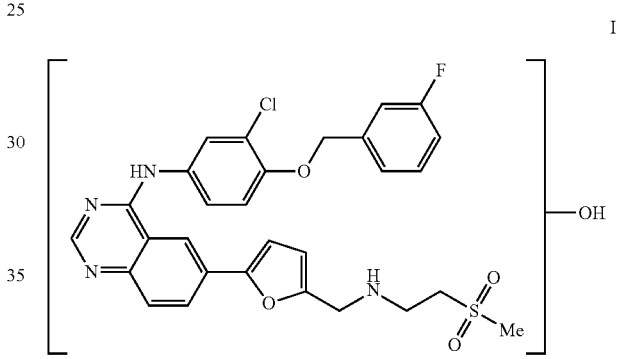

In some additional embodiments, the present invention provides a compound of formula II wherein a nitrogen atom on a heteroaryl group is oxidized to give the N-oxide that is chemically stable (i.e., does not spontaneously degrade).

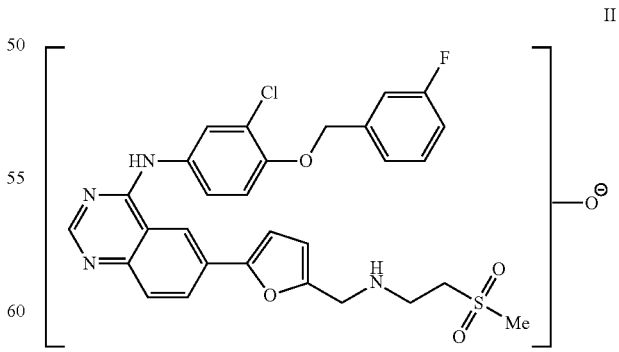

In some further embodiments, the present invention provides a compound of formula III, which is prepared from a compound of type I or II or inspired by a compound of formula I or II.

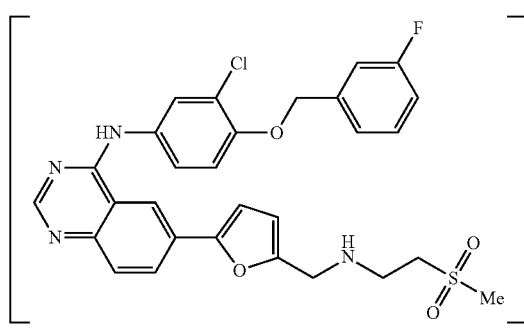
In some embodiments, the present invention provides compounds with the following formulae:
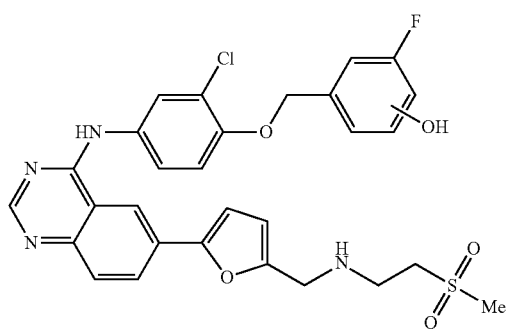
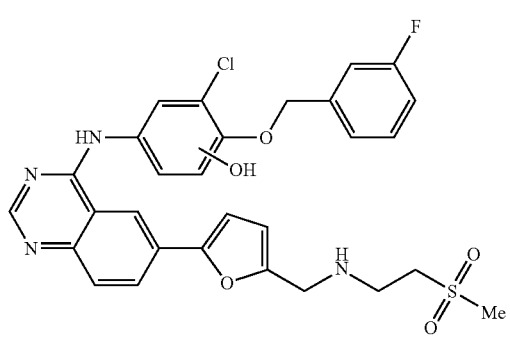
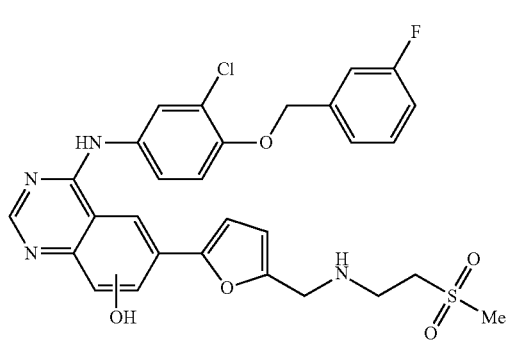
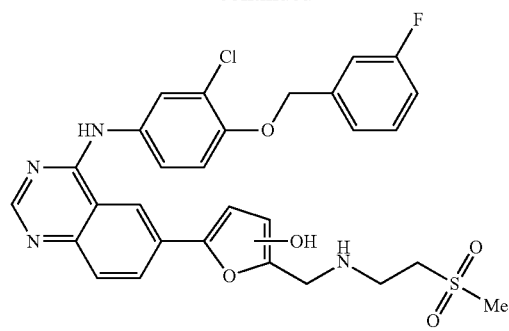
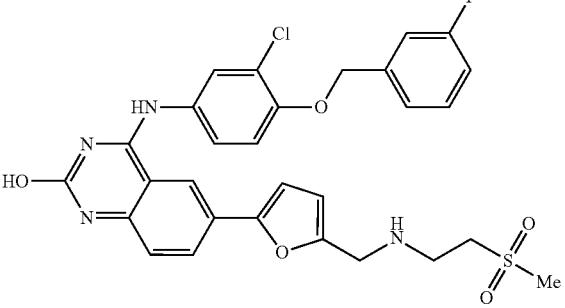
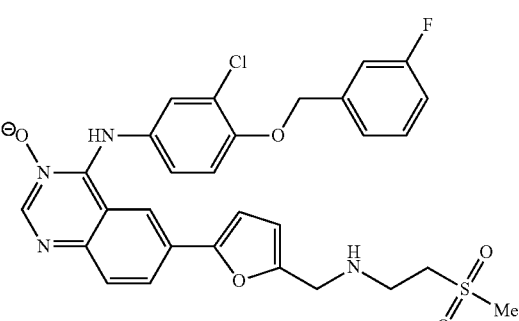
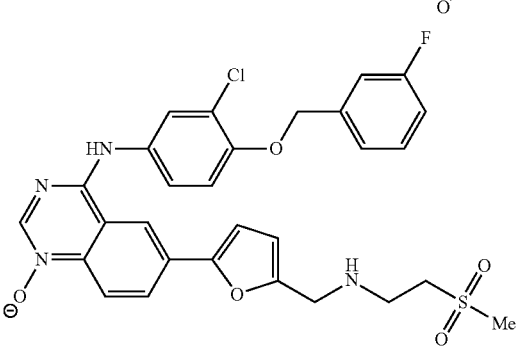
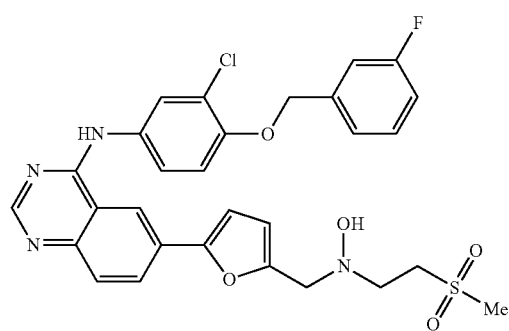

-continued

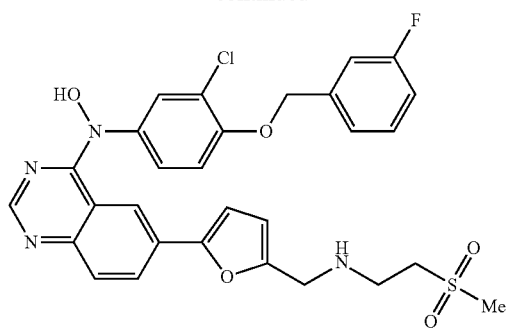

In some additional embodiments, the present invention provides compounds with the following formulae:

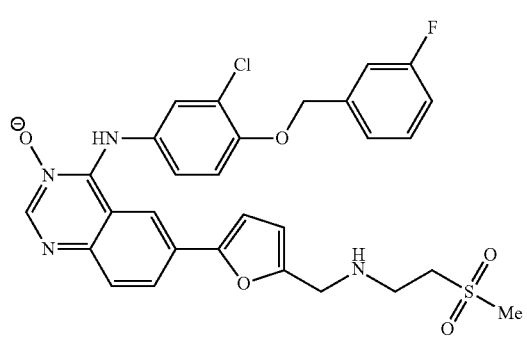

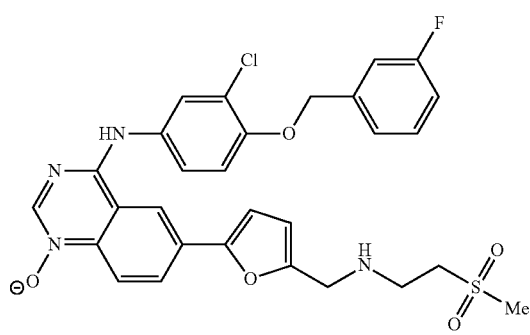

In some further embodiments, the present invention provides a compound of formula III which is prepared from a compound of type I or II or derived from a compound of formula I or II, wherein R is optionally substituted alkyl, alkenyl, alkynyl, cycloalkyl, cycloalkylalkyl, aryl, arylalkyl, heteroaryl, heteroarylalkyl, heteroalkyl, heteroalkylaryl, alkoxy, aryloxy, carboxy, carbonyloxy, carboxyalkyl, substituted carbonyl, amino, substituted amino, aminoalkyl, halo, haloalkyl, hydroxyalkyl, thio, alkylthio, or sulfonyl.

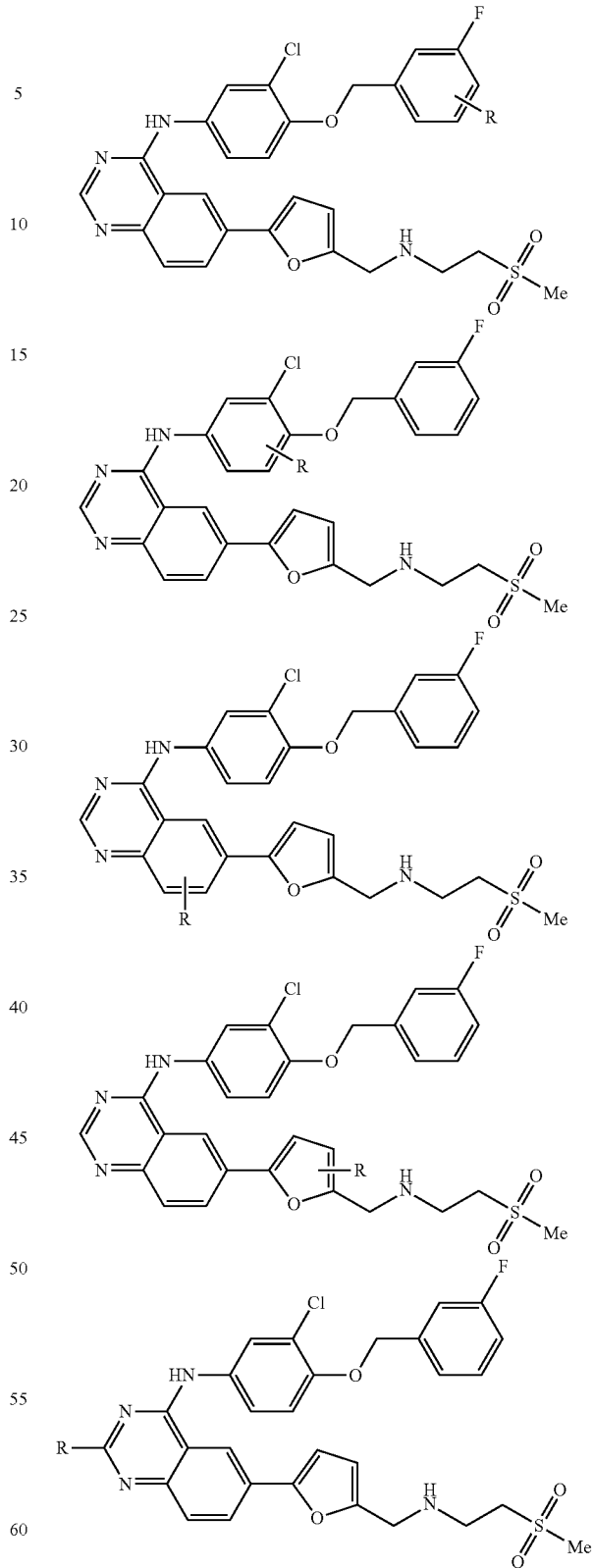

In some embodiments, the present invention provides compounds with the following formulae, wherein R is alkyl, cycloalkyl, cycloalkylalkyl, aryl, arylalkyl, heteroaryl, heteroarylalkyl, heteroalkyl, heteroalkylaryl, alkoxy, aryloxy, carboxyalkyl, carbonyloxy, substituted carbonyl, amino, substituted amino, aminoalkyl, haloalkyl, hydroxyalkyl, or sulfonyl.

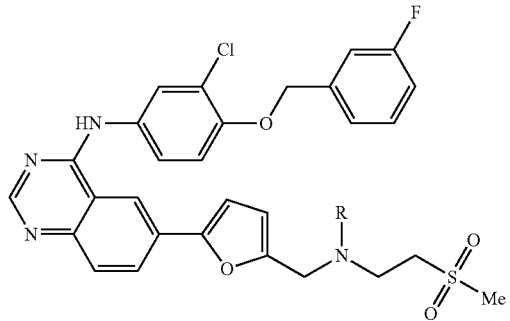

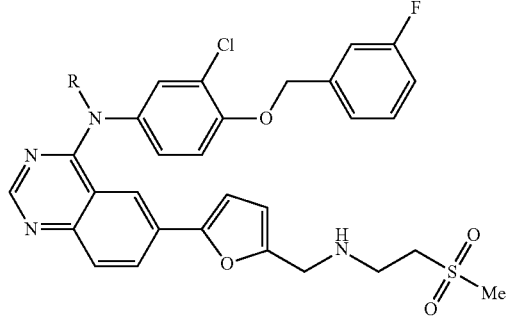

In still some further embodiments, the present invention provides compounds with the following formulae:

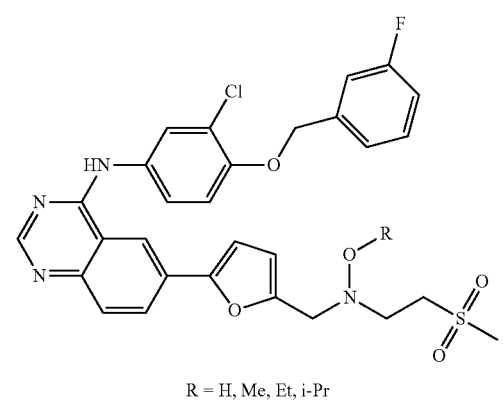

R = H, Me, Et, i-Pr

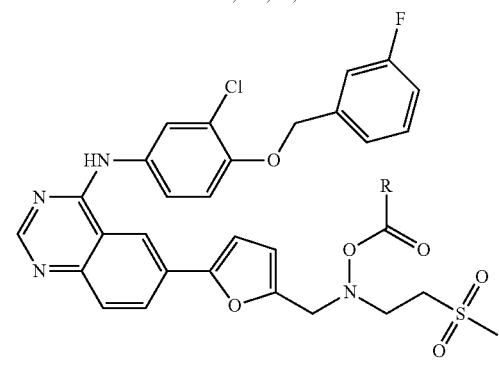

R = H, Me, Et, i-Pr, c-Pr, c-Bu, Ph,
4-F—Ph, 2-imidazolyl

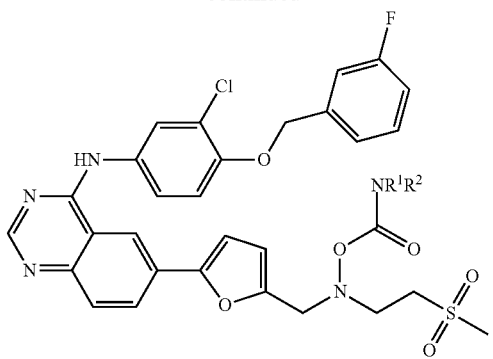

$R^1R^2$ = H, Me; H, $F_3CCH_2$; Me, Me;
$(CH_2)_3$, $(CH_2)_4$

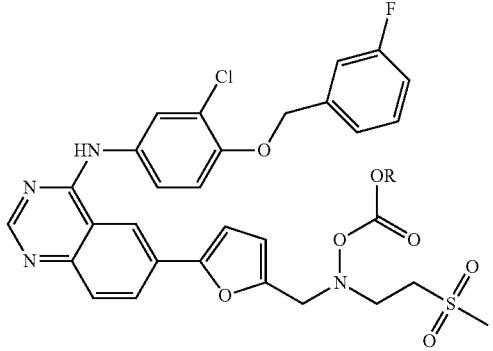

R = Me, Et, i-Pr, c-Pr, c-Bu

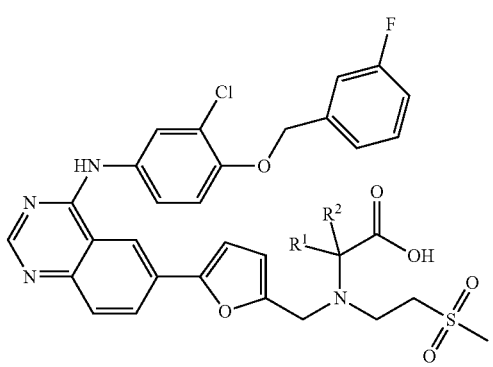

$R^1R^2$ = H, Me; H, i-Pr; H, c-Pr, c-Bu; Me, Me;
$(CH_2)_3$; $(CH_2)_4$; $(CH_2OCH_2)$; H, $CF_3$

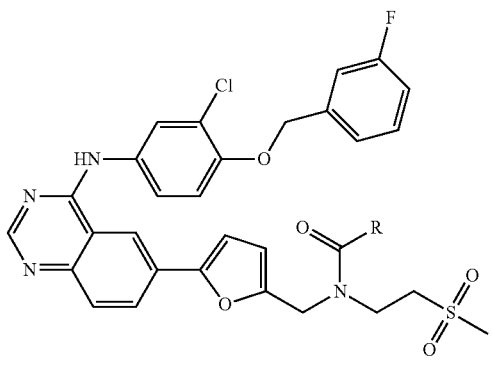

R = H, Me, Et, i-Pr, c-Pr, c-Bu, Ph,
4-F—Ph, 2-imidazolyl

-continued

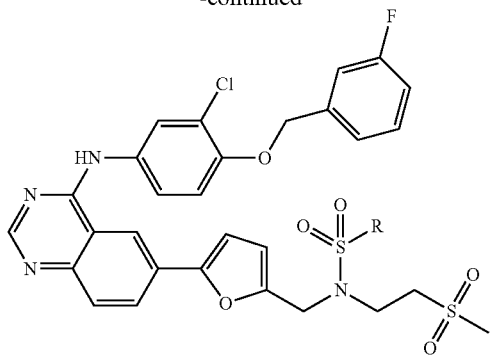

R = H, Me, Et, i-Pr, c-Pr, c-Bu, Ph,
4-F—Ph, 2-imidazolyl

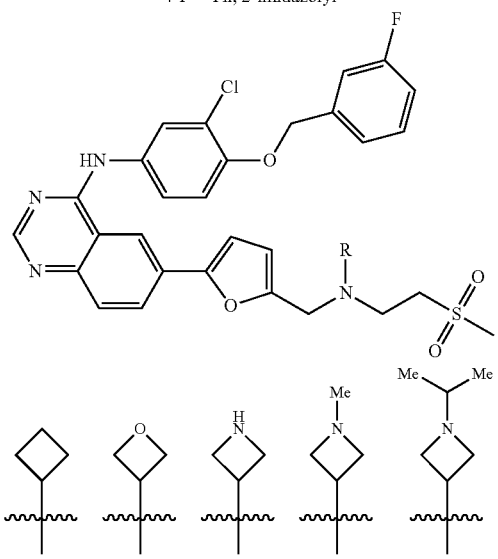

The present invention provides lapatinib analogs with improved properties, such as improved efficacy, pharmacokinetics, safety, and specificity. In some embodiments, the present invention provides lapatinib analogs that provide therapeutic benefits. In particular, in some embodiments, the present invention provides lapatinib analogs that provide increased binding to ERBB2, reduced clearance, longer half lives, favorable distributions, and/or improved bioavailability. In some additional embodiments, the present invention provides lapatinib analogs with improved safety factors (e.g., no interaction with undesirable targets, such as hERG, liver CYPS, etc.), differentiated kinase specificity, etc. In some embodiments, the present invention provides lapatinib analogs with improved efficacy and safety relative to lapatinib.

Historically, pharmaceutical companies have been challenged to maintain their drug pipelines, particularly in view of the pressure placed on drug discovery and development for environmentally-friendly methods and compositions, increasing cost-constraints on healthcare systems, and demanding regulatory requirements. Thus, there remains a need in the art for cost-effective, sustainable methods for the discovery and development of new and/or improved drugs (See e.g., Paul et al., Nat. Rev. Drug Disc., 9:203-214 [2010]). Indeed, innovation in synthetic methods has the ability to drive the expansion of drug pipelines (e.g., palladium catalyzed reaction). Late stage functionalization of completed drug candidate scaffolds has been investigated for the generation of chemical diversity. Fluorination and oxidation are two transformations that have found the most use.

In contrast, the present invention provides methods and compositions utilizing enzymes for the synthesis and development of new drug candidates. Enzymes provide the means to generate great structural diversity, facilitating investigations into the compounds' efficacy and safety. These methods are environmentally friendly, sustainable, and cost-effective.

During the development of the present invention, a specific isoform of the cytochrome P450 monooxygenases, namely the enzyme from *Bacillus megaterium* (BM3) was used. Oxidation of a biologically active small molecule by cytochrome P450 monooxygenase BM3 or related enzymes was used to generate closely related drug analogs, some of which have improved activity and/or diminished unfavorable characteristics relative to the parent drug. Furthermore, the addition of a hydroxyl group in some of the analogs provides a functional handle for creating addition analogs.

Lapatinib (1, Table 1) is a dual EGFR and ErbB2 inhibitor. As described in the Examples, it was tested against the kinases EGFR, ErbB4 and Syk. MCYP0038 (Codexis, Redwood City, Calif.) oxidized lapatinib at one of the two secondary amines to give the hydroxylamine 2. This compound showed an approximately 3-fold decrease in activity against both EGFR and ErbB4 relative to lapatinib.

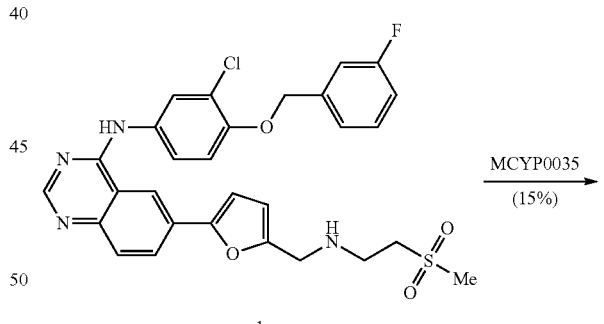

1

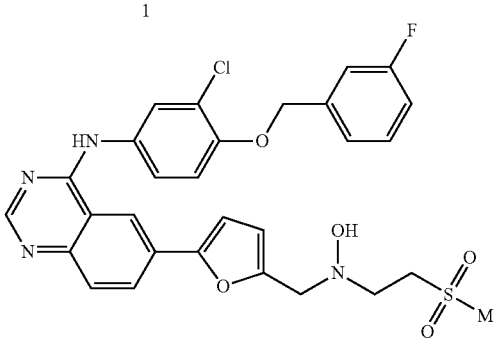

2

TABLE 1

EGFR, ErbB4, and Syc inhibition for compounds 1 and 2.

| compd | R | EGFR IC$_{50}$ | ErbB4 IC$_{50}$ | Syk IC$_{50}$ |
|---|---|---|---|---|
| 1 | H | 22 | 13 | >10,000 |
| 2 | OH | 72 | 32 | >10,000 |

Lapatinib has a boxed warning describing severe liver toxicity. Thus, the present invention provides analogs that mitigate this risk and also provide efficacy improvements, as compared to lapatinib. In some embodiments, preclinical testing to measure liver toxicity is conducted in rodent toxicity studies. Lapatininb is also a CYP3A4 inhibitor and time-dependent inhibitor. Although it is not intended that the present invention be limited to any specific mechanism and/or theory, it is possible that time dependent inhibition is caused by formation of a reactive metabolite and this reactive metabolite might cause liver toxicity. Thus, CYP3A4 inhibition was investigated.

Based on the result for lapatinib analog 2, two further types of analogs were prepared. The first type of analogs were derivatives of the hydroxyl amine created by reacting the hydroxyl group with a nucleophile (Scheme 1). The carbamate (3) was prepared from the hydroxylamine by reaction with potassium isocyanate in the presence of acid. Analog 2 was converted to dimethylcarbamate (4) by reaction with carbamoyl chloride and converted to methylcarbonate (5) in a reaction with methylchloroformate. The second type of analogs were prepared directly from lapatinib by using the amine nitrogen as a nucleophile (See, Scheme 2, below).

Scheme 1. Analog Synthesis.

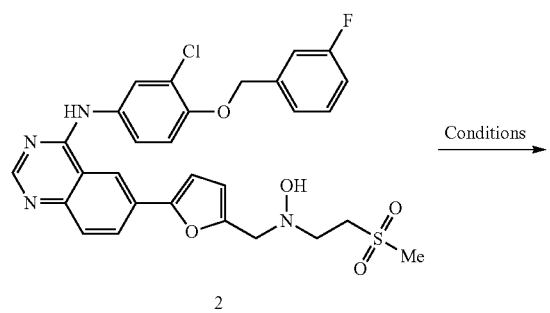 [SMILES: CS(=O)(=O)CCN(O)Cc1ccc(-c2ccc3ncnc(Nc4ccc(OCc5cccc(F)c5)c(Cl)c4)c3c2)o1]

| compd | Conditions | R |
|---|---|---|
| 3 | NCOK, HCl, H$_2$O, THF, 0° C., 4 h | —C(O)NH$_2$ |
| 4 | Me$_2$NCOCl, pyr, rt, 20 h | —C(O)NMe$_2$ |
| 5 | MeOCOCl, TEA, THF, rt, 2 h | —C(O)OMe |

Reactions used to prepare the second set of lapatinib analogs included alkylation, sulfonylation, acylation and reductive amination (Scheme 2, below). The rationale for preparing these analogs was to create a significant amount of chemical diversity in a small number of analogs. Alkylation with t-butyl bromoacetate followed by removal of the t-butyl group with TFA gave amino acid (6). Sulfonylation with mesyl chloride gave sulfonamide (7) and acylation with acetyl chloride gave acetamide (8). Reductive amination was used to make a series of amines (9-12). In the case of 12, the Boc-protected aminoketone was coupled with lapatinib and the Boc group removed by acidic hydrolysis. Alkylation with methyl bromoacetate gave the amino acid methyl ester (13).

Scheme 2.

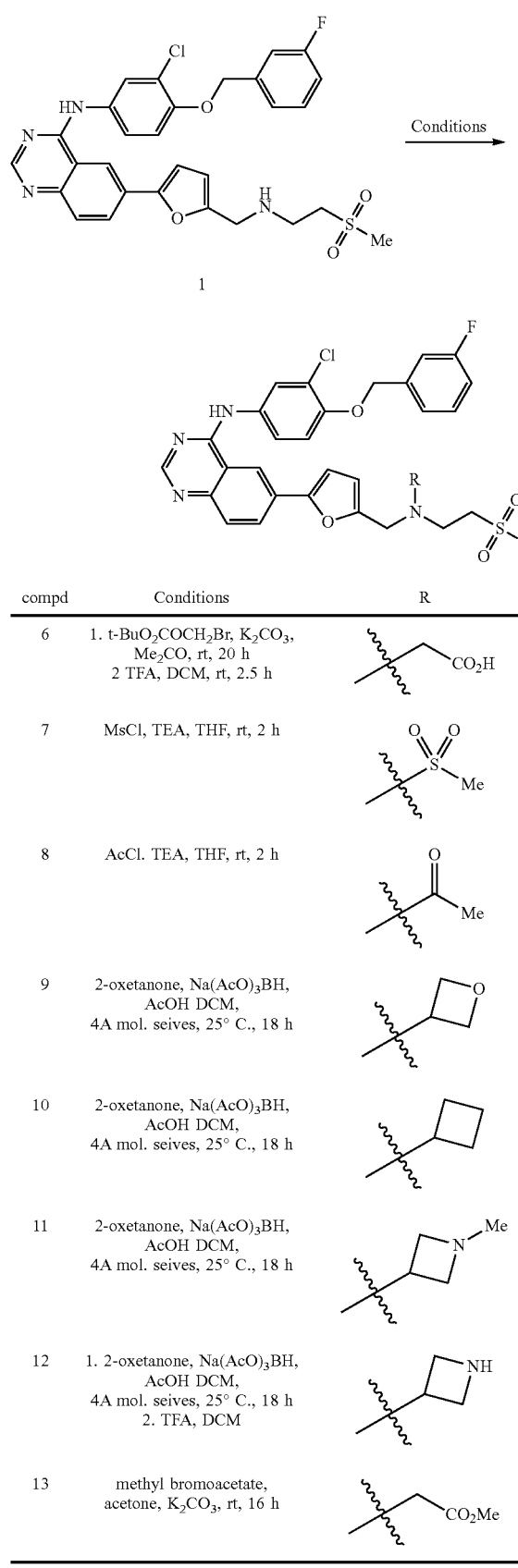

| compd | Conditions | R |
|---|---|---|
| 6 | 1. t-BuO$_2$COCH$_2$Br, K$_2$CO$_3$, Me$_2$CO, rt, 20 h<br>2 TFA, DCM, rt, 2.5 h | –CO$_2$H |
| 7 | MsCl, TEA, THF, rt, 2 h | –S(O)$_2$Me |
| 8 | AcCl. TEA, THF, rt, 2 h | –C(O)Me |
| 9 | 2-oxetanone, Na(AcO)$_3$BH, AcOH DCM, 4A mol. seives, 25° C., 18 h | oxetanyl |
| 10 | 2-oxetanone, Na(AcO)$_3$BH, AcOH DCM, 4A mol. seives, 25° C., 18 h | cyclobutyl |
| 11 | 2-oxetanone, Na(AcO)$_3$BH, AcOH DCM, 4A mol. seives, 25° C., 18 h | N-methylazetidinyl |
| 12 | 1. 2-oxetanone, Na(AcO)$_3$BH, AcOH DCM, 4A mol. seives, 25° C., 18 h<br>2. TFA, DCM | azetidinyl (NH) |
| 13 | methyl bromoacetate, acetone, K$_2$CO$_3$, rt, 16 h | –CO$_2$Me |

The analogs were tested against the two therapeutic targets of lapatinib, ErbB2 and EGFR. They were also tested for CYP3A4 inhibition and time dependent inhibition, since these are important safety issues for lapatinib (Table 3-1, in Example 3). Time-dependent inhibition of CYP3A4 was determined by measuring human liver microsome metabolism of midazolam after 30 min in two study arms. In the first arm (non-time dependent), the test compounds were preincubated with microsomes before the addition of midazolam and NAHPH at t=0 of the metabolism study. In the second arm (time dependent), NADPH was included in the preincubation step prior to the addition of midazolam at t=0. The first arm is reported as the CYP 3A4 IC$_{50}$ in Table 3-1, and the second arm is reported as the time dependent CYP3A4 IC$_{50}$. Compounds with a CYP3A4 IC$_{50}$: time-dependent CYP3A4 IC$_{50}$ of ≥2 were considered time-dependent inhibitors. Six of the 8 new compounds (5-10) inhibited ErbB2 or EGFR with better potency than lapatinib; 5 compounds were less potent CYP3A4 inhibitors (3, 4, 6, 7, and 10); 7 of the 8 new compounds were less potent CYP3A4 inhibitors after preincubation with the test compound (3, 4; 6-10). All of the compounds also showed less of a time dependent shift, with the possible exception of 10.

The biocatalytic production of these compounds enabled the rapid identification of new kinase inhibitor leads. With its structure known, it was it was now possible to chemically synthesize analog 2. Scheme 3 shows the chemical synthesis of lapatinib analog 2 using oxone, in the presence of potassium carbonate.

Scheme 3:

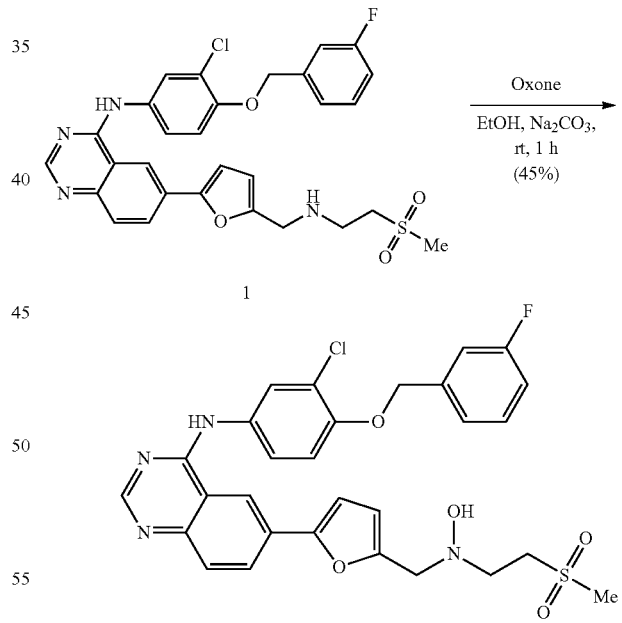

As indicated in the Examples, these lapatinib analogs exhibited superior efficacy and better safety profiles than lapatinib. Thus, it is contemplated that one or more of these analogs find use in the pharmaceutical treatment of cancer.

Pharmaceutical formulations comprising the lapatinib analogs of the present invention can be administered in the form of dosage units comprising a predetermined amount of active ingredient per dosage unit. The dosage unit may depend upon the condition being treated, the method of administration and the age, weight and condition of the patient, etc., factors which are known to those of skill in the art. In some embodiments, dosage unit formulations comprise a daily dose, part-dose (i.e., partial dose), or a corresponding fraction thereof of an active ingredient. It is intended that the pharmaceutical formulations comprising the lapatinib analogs of the present invention are prepared using processes generally known in the pharmaceutical arts.

The foregoing and other aspects of the invention may be better understood in connection with the following non-limiting Examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and μM (micromolar); nM (nanomolar); pM (picomolar); mol (moles); gm and g (gram); mg (milligrams); ug and μg (micrograms); L and l (liter); ml and mL (milliliter); ul, uL, μL, and μl (microliter); cm (centimeters); mm (millimeters); um and μm (micrometers); sec. and "'" (i.e., quote symbol) (seconds); min(s) and "'" (i.e., an apostrophe) (minute(s)); h(s) and hr(s) (hour(s)); U (units); MW (molecular weight); rpm (rotations per minute); rt and r.t. (room temperature); ° C. (degrees Centigrade); sat.aq. (saturated aqueous); DNA (deoxyribonucleic acid); RNA (ribonucleic acid); HPLC (high pressure liquid chromatography); prep-HPLC (preparative HPLC); LCMS (liquid chromatography mass spectrometry); TLC (thin layer chromatography); EtOH (ethanol); TEA (triethylamine, triethanolamine, N,N-diethylethanamine, N,N,N-triethylamine, (diethylamino)ethane); TFA (trifluoroacetic acid); THF (tetrahydrofuran, oxolane, 1,2-epoxybutane, butylene oxide, cyclotetramethylene oxide, oxacyclopentane, diethylene oxide, furanidine, hydrofuran, tetra-methylene oxide); DCM (dichloromethane, methylene chloride, methylene dichloride); AcCl (acetyl chloride, ethanoyl chloride, acyl chloride); AcOH (acetic acid); MeCl (methanesulfonyl chloride, mesyl chloride); EA (ethyl acetate, ethyl ethanoate, EtOAc); Et$_2$O (diethyl ether, ethyl ether, sulfuric ether, ether, ethoxyethane, ethyl oxide, 3-oxapentane,); 4AM.S. (4 Angstrom molecular sieve); IC$_{50}$ (50% inhibitory concentration [i.e., the concentration at which 50% of the cells' growth is inhibited]); CRO (contract research organization); ATCC (American Type Culture Collection, Manassas, Va.); Codexis (Codexis, Inc., Redwood City, Calif.); Emeryville Pharmaceutical (Emeryville Pharmaceutical Services, Emeryville, Calif.); Promega (Promega, Inc., Madison, Wis.); GraphPad (GraphPad Software, Inc., La Jolla, Calif.); Calbiochem (Calbiochem, available from EMD Millipore Corp., Billerica, Mass.); NEB (New England Biolabs, Ipswich, Mass.); Sigma-Aldrich (Sigma-Aldrich, St. Louis, Mo.; Invitrogen (Invitrogen, Life Technologies, Grand Island, N.Y.); Stratagene (Stratagene, now an Agilent Technologies company); Agilent (Agilent Technologies, Inc., Santa Clara, Calif.); Molecular Devices (Molecular Devices, Sunnyvale, Calif.); USBio (US Biological, Swampscott, Mass.); Qiagen (Qiagen Inc., Germantown, Md.); Anhui (Anhui Sanxing Resin Technology Co., Ltd. China); BD (Becton Dickinson & Company, Franklin Lakes, N.J.); Perkin Elmer (Perkin Elmer, Santa Clara, Calif.) Bio-Rad (Bio-Rad Laboratories, Hercules, Calif.); ACME (ACME Bioscience, Inc., Palo Alto, Calif.); and RBC (Reaction Biology Corporation, Malvern Pa.).

Example 1

MCYP Screening Procedure

MCYP Screening Procedure

Lapatinib and lapatanib analogs were screened using a MCYP panel comprising a set of 96 different recombinant cytochrome P450 monooxygenases (Codexis) using the standard protocol provided with the panel. The resulting samples were analyzed by LC/MS with a Finnigan LXQ ion trap Mass Spectrometer.

Data Analysis Procedure

LC/MS/MS chromatograms were visually inspected for the parent peak for lapatinib. Ion extraction was performed for M+1 of the parent drug and M+1+16 to identify any mono-oxidized products. The masses of any other peaks >5% in the UV chromatogram or the TLC chromatogram were noted. The data for all the 96 wells were then analyzed using the parent drug mass and any products detected during the qualitative analysis. Conversion was determined as the sum of the product peak areas divided by the total peak areas.

Example 2

Preparation of Lapatanib Analogs

Various lapatanib analogs were prepared using standard synthetic chemistry, as described herein. Lapatinib was prepared in the following manner:

Biocatalytic Synthesis:

MicroCYP buffer mix (5.6 g) was dissolved in water (195 ml). The enzyme MCYP0038 (723 mg) was added to the buffer and water mixture. The mixture was shaken to form a light yellow suspension. The substrate, lapatinib (150 mg) was dissolved in DMSO (5 ml), which was added to the above solution to give a cloudy suspension. The solution was incubated at 30° C., 110 rpm and after 4 hours, a sample was taken for LCMS analysis. In this experiment, 11% product was obtained and 80% starting material remained. Incubation of the reactions was continued for another 20 hours. LCMS analysis at this timepoint showed that 15% product was obtained and 74% starting material remained.

The resulting solution was diluted with MeOH (100 mL) and poured onto D101 resin (75 g; Anhui) to remove protein and buffer components. The resin was washed with water (3 L) followed by MeOH (3 L). The MeOH eluent was collected and evaporated, resulting in a crude product. The residue was further purified by HPLC to produce compound 2 as a light yellow solid.

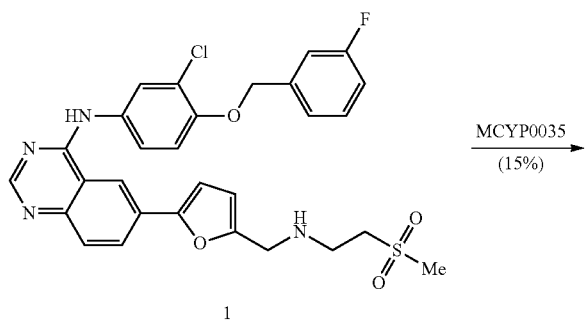

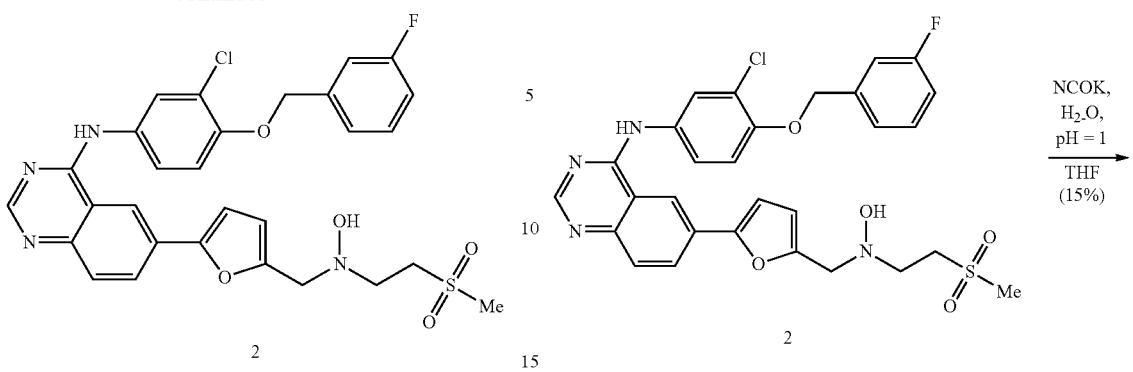

Chemical Synthesis of Compound 2:

First, lapatinib (1, 200 mg, 0.35 mmol) was dissolved in EtOH (200 ml). Then, $Na_2CO_3$ (240 mg, 2.26 mmol) and oxone (1000 mg, 1.63 mmol) were added to the solution. After 15 hours under vigorous stirring at room temperature a sample was analyzed using LCMS. The results indicated that 40% of product was obtained. Water (800 ml) was added to quench the reaction and the product was extracted with diethylether. The organic layer was concentrated and the residue was purified by preparative-HPLC to produce compound 2 (70 mg, 35%).

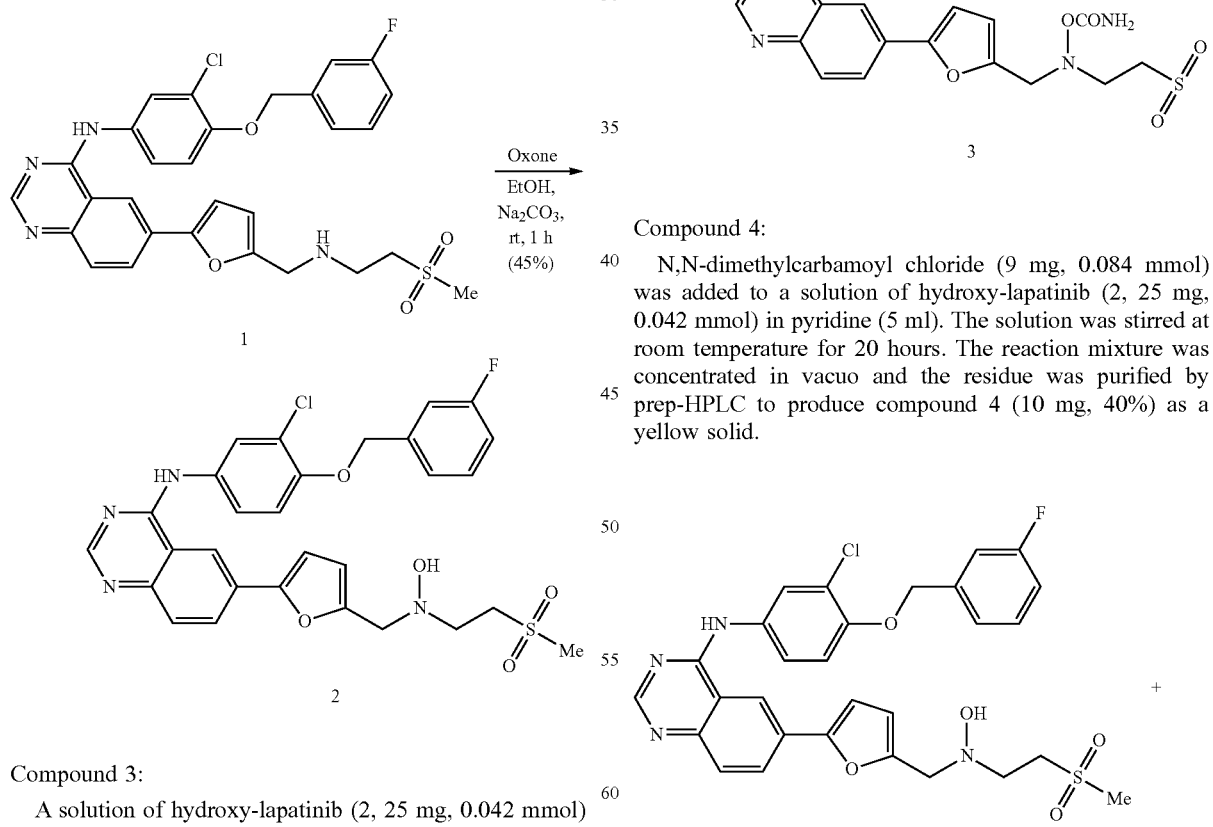

Compound 3:

A solution of hydroxy-lapatinib (2, 25 mg, 0.042 mmol) and potassium isocyanate (NCOK; 7 mg, 0.086 mmol) in $THF-H_2O$ was brought to pH 1 with concentrated HCl. The solution was stirred at 0° C. for 2 hours and concentrated in vacuo and the residue purified by prep-HPLC, using standard methods known in the art, to produce compound 3 (8 mg, 32%) as a yellow solid.

Compound 4:

N,N-dimethylcarbamoyl chloride (9 mg, 0.084 mmol) was added to a solution of hydroxy-lapatinib (2, 25 mg, 0.042 mmol) in pyridine (5 ml). The solution was stirred at room temperature for 20 hours. The reaction mixture was concentrated in vacuo and the residue was purified by prep-HPLC to produce compound 4 (10 mg, 40%) as a yellow solid.

-continued

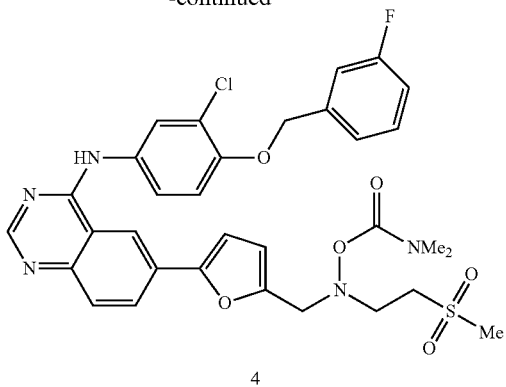

4

Compound 5:

Methylchloroformate (6.49 mg, 0.069 mmol) was added drop-wise to a stirred solution of hydroxy-lapatinib (2, 40 mg, 0.069 mmol) and TEA (7.0 mg, 0.069 mmol) in THF (5 mL) at 0° C. The mixture was stirred at room temperature for 2 h. The mixture was diluted with ethylacetate (10 mL) and water (5 mL). The organic layer was washed with brine (5 mL), dried over $Na_2SO_4$, and concentrated. The residue was purified by prep-HPLC to give compound 5 (13 mg, 29%) as a yellow solid.

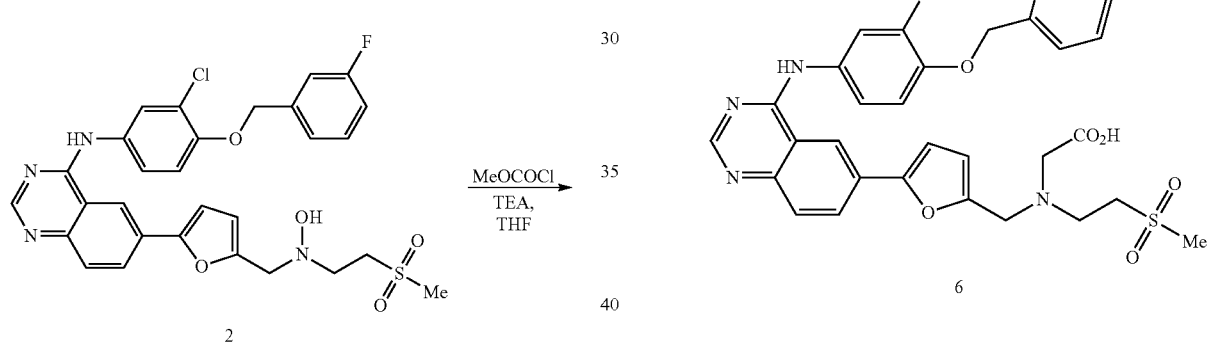

Compound 6:

$K_2CO_3$ (6 mg, 0.043 mmol) was added to a solution of lapatinib (1, 25 mg, 0.043 mmol) and bromoacetic acid tert-butyl ester (16 mg, 0.085 mmol) in acetone (5 ml). The mixture was stirred at room temperature for 20 hours. The mixture solution was then concentrated in vacuo and the residue dissolved in dichloromethane (5 ml), TFA (0.5 ml) was added and the solution was stirred at room temperature for 2.5 hours. The solution was concentrated in vacuo after which the residue was purified by prep-HPLC to produce compound 6 (3 mg, 12%) as a yellow solid.

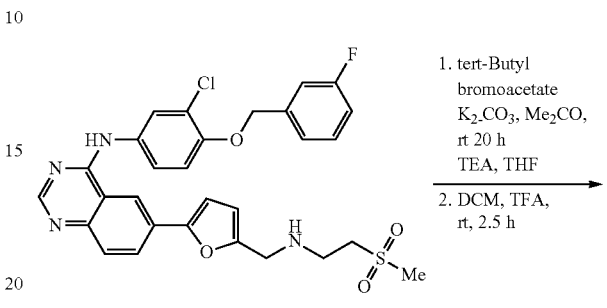

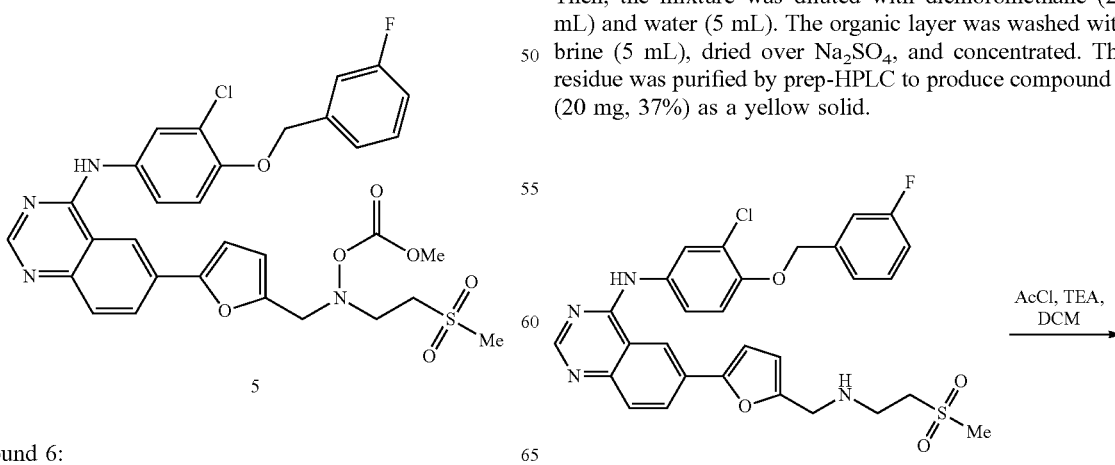

Compound 8:

Acetylchloride (8.05 mg, 0.10 mmol) was added dropwise to a stirred solution of lapatinib (1, 50 mg, 0.086 mmol) and TEA (10.4 mg, 0.10 mmol) in dichloromethane (5 mL), at 0° C. The mixture was stirred at room temperature for 1 h. Then, the mixture was diluted with dichloromethane (20 mL) and water (5 mL). The organic layer was washed with brine (5 mL), dried over $Na_2SO_4$, and concentrated. The residue was purified by prep-HPLC to produce compound 8 (20 mg, 37%) as a yellow solid.

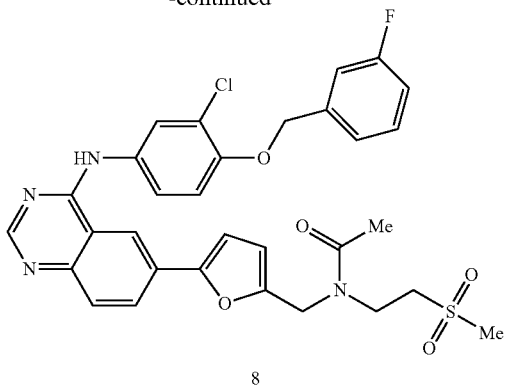

8

Compound 7:

Mesyl chloride (11.5 mg, 0.10 mmol) was added dropwise to a stirred solution of lapatinib (1, 50 mg, 0.086 mmol) and TEA (10.4 mg, 0.10 mmol) in dichloromethane (5 mL), at 0° C. The mixture was stirred at room temperature for 1 h. Then, the mixture was diluted with dichloromethane (20 mL) and water (5 mL). The organic layer was washed with brine (5 mL), dried over $Na_2SO_4$, and concentrated. The residue was purified by prep-HPLC to produce compound 7 (12 mg, 21%) as a yellow solid.

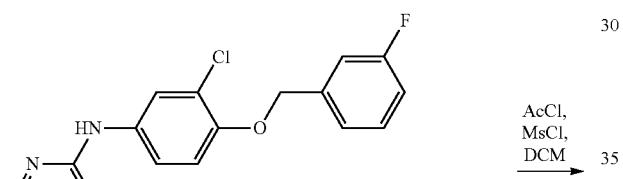

1

AcCl, MsCl, DCM

7

Compound 9:

A solution of lapatinib (1, 50 mg, 0.086 mmol) and 3-oxetanone (12.05 mg, 0.172 mmol) in dichloromethane (10 mL) was added to a flask containing activated 4 A molecular sieves (57.4 mg). Acetic acid (0.003 mL, 0.003 mg, 0.043 mmol) was added and the mixture was stirred at room temperature for 2 h, then $NaBH(OAc)_3$ (36.5 mg, 0.172 mmol) was added and the reaction mixture was stirred for an additional 18 h at 25° C. The mixture was then partitioned between dichloromethane and a saturated aqueous solution of $NaHCO_3$. The aqueous phase was back-extracted with additional dichloromethane and the combined organic phases were dried over $Na_2SO_4$, filtered, and concentrated to provide crude product. The residue was purified by prep-HPLC to produce compound 9 (25 mg, 45%) as a yellow solid.

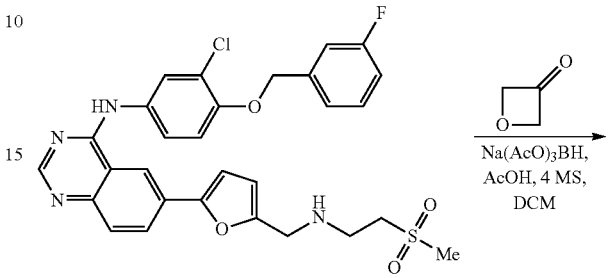

1

Na(AcO)₃BH, AcOH, 4 MS, DCM

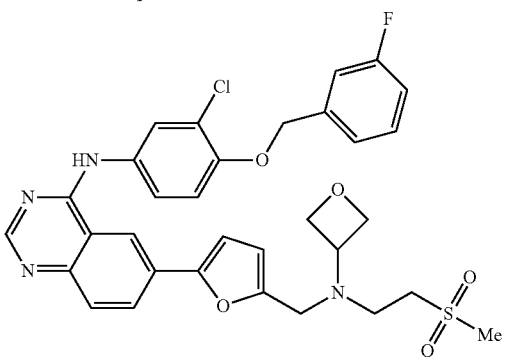

9

Compound 10:

A solution of lapatinib (1, 50 mg, 0.086 mmol) and cyclobutanone (12.04 mg, 0.172 mmol) in dichloromethane (10 mL) was added to a flask containing activated 4 A molecular sieves (57.4 mg). Acetic acid (0.003 mL, 0.003 mg, 0.043 mmol) was added and the mixture was stirred at room temperature for 2 h, then $NaBH(OAc)_3$ (36.5 mg, 0.172 mmol) was added and the reaction mixture was stirred for an additional 18 h at 25° C. The mixture was then partitioned between dichloromethane and a saturated aqueous solution of $NaHCO_3$. The aqueous phase was back-extracted with additional dichloromethane and the combined organic phases were dried over $Na_2SO_4$, filtered, and concentrated to provide crude product. The residue was purified by Prep-HPLC to produce compound 10 (25 mg, 45.8%) as a yellow solid.

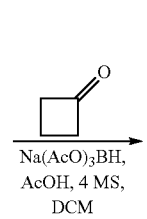

Na(AcO)₃BH, AcOH, 4 MS, DCM

1

-continued

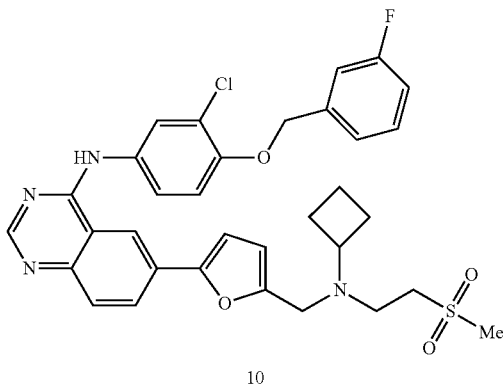

10

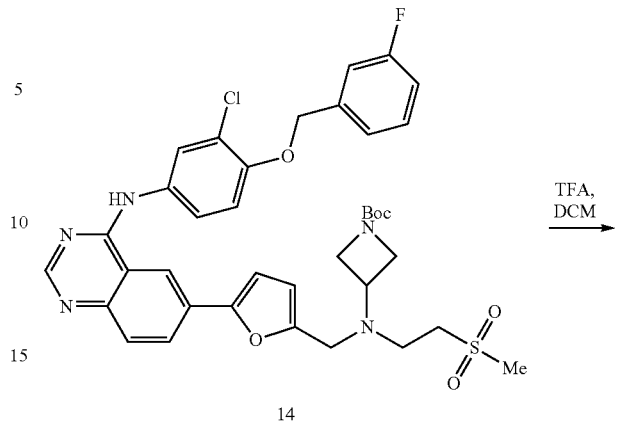

14

Compound 12:

A solution of lapatinib (1, 50 mg, 0.086 mmol) and Boc-3-azetidinone (29.4 mg, 0.172 mmol) in dichloromethane (10 mL) was added to a flask containing activated 4 A molecular sieves (57.4 mg). Acetic acid (0.003 mL, 0.003 mg, 0.043 mmol) was added and the mixture was stirred at room temperature for 2 h, then NaBH(OAc)$_3$ (36.5 mg, 0.172 mmol) was added and the reaction mixture was stirred for an additional 18 h at 25° C. The mixture was then partitioned between dichloromethane and a saturated aqueous solution of NaHCO$_3$. The aqueous phase was back-extracted with additional dichloromethane and the combined organic phases were dried over Na$_2$SO$_4$, filtered, and concentrated to provide crude compound 14. The residue was purified by prep-HPLC to produce compound 12 (40 mg, 63%) as a yellow solid.

Trifluoroacetic acid (0.003 mL, 0.041 mmol) was added to a solution of compound 13 (20 mg, 0.027 mmol) in dichloromethane (5 mL), and the resulting mixture was stirred at room temperature for 30 min. Additional trifluoroacetic acid (0.0015 mL, 0.022 mmol) was added and resulting mixture was stirred at room temperature for 60 min. A solution of trifluoroacetic acid (0.003 mL, 0.041 mmol) in dichloromethane (1 mL) was added and stirring was continued for 60 min, then a fourth portion of trifluoroacetic acid (0.003 mL, 0.022 mmol) was added and resulting mixture was stirred for 60 min. The mixture was adjusted to pH=7 with saturated aqueous NaHCO3 and extracted with dichloromethane (three times, 10 mL). The combined organic phases were dried over Na$_2$SO$_4$, filtered, and concentrated to provide crude product. The residue was purified by prep-HPLC to produce compound 12 (11 mg, 64%) as a yellow solid.

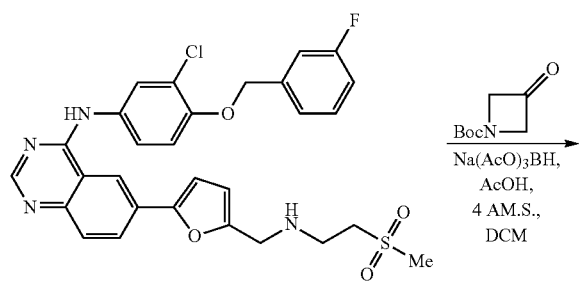

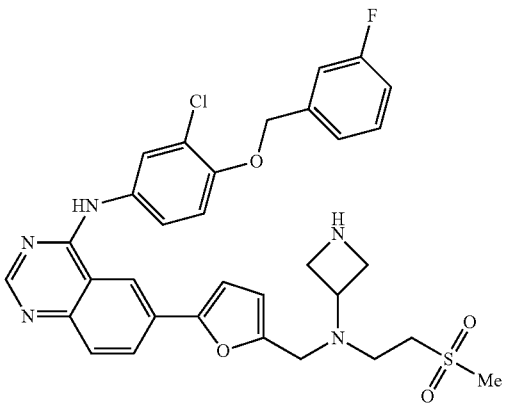

12

Compound 11:

A solution of crude compound 1 (20 mg, 0.031 mmol) in dichloromethane (5 mL) and acetic acid (0.02 mL, 0.35 mmol) was stirred at room temperature with sequential addition of 37% aqueous formaldehyde (0.005 mL, 0.062 mmol) and NaBH(OAc)$_3$ (13.2 mg, 0.062 mmol). The reaction mixture was stirred for 4 h, and then partitioned between dichloromethane and a saturated aqueous solution of NaHCO$_3$. The aqueous phase was back-extracted with additional dichloromethane. The combined organic phases were dried over Na$_2$SO$_4$, filtered, and concentrated. The residue was purified by prep-HPLC to produce compound 11 (13 mg, 65%) as a yellow solid.

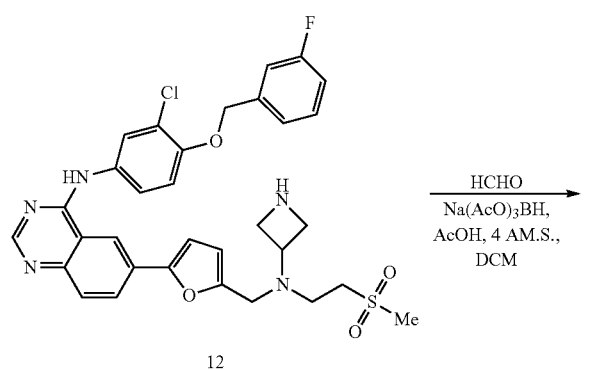

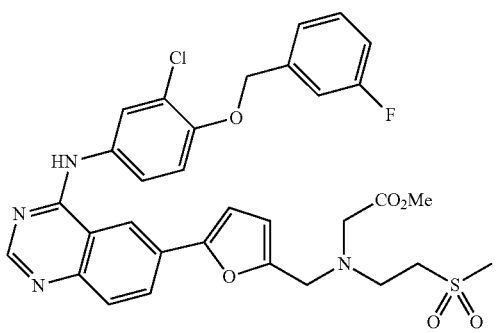

Example 3

Biochemical Testing of Analogs

The lapatanib analogs prepared as described in Example 2 were tested for their inhibition of human EGFR, human ErbB2, and CYP3A4.

Assay Protocols

Kinase assays were performed using standard protocols known to those skilled in the art. In brief, kinase, peptide substrate labeled with both coumarin (donor fluorophore) and fluorescein (acceptor fluorophore), ATP, and test compound are incubated together in a kinase reaction buffer. Typically, the reaction was stopped by development reagent (protease) with certain dilution factor after 2 hours. The plate was analyzed in Perkin Elmer Envision by FRET mode. The high ratio of coumarin/fluorescein represents 0% phosphorylation rate while low ratio of coumarin/fluorescein represents 100% phosphorylation rate.

CYP3A4 inhibition and time-dependent inhibition of CYP3A4 were determined using pooled human liver microsomes (HLM, BD Gentest, Cat No.: 452117, Lot No.: 38290) and methods known to those skilled in the art.

Assay Results

As shown in Table 3-1, six of the eight compounds tested (5, 6, 8, 7, 9 and 10) inhibited ErbB2 or EGFR with better potency than lapatinib; five of the tested compounds were less potent CYP3A4 inhibitors (3, 4, 6, 7, and 10); seven of the compounds were less potent CYP3A4 inhibitors after preincubation with the test compound (3, 4, 6, 7, 8, 9, and 10). All of the compounds also showed less of a time dependent shift with the possible exception of compound 10.

Compound 13:

To a solution of compound 1 (100 mg, 0.17 mmol, 1.0 eq) and methyl bromoacetate (52 mg, 0.34 mmol, 2.0 eq) in acetone (5 mL) was added potassium carbonate (24 mg, 0.17 mmol, 1.0 eq). The reaction mixture was stirred at room temperature for 16 h, filtered, and concentrated. The residue was purified by prep-HPLC to produce compound 14 (45 mg, 40%) as a yellow solid.

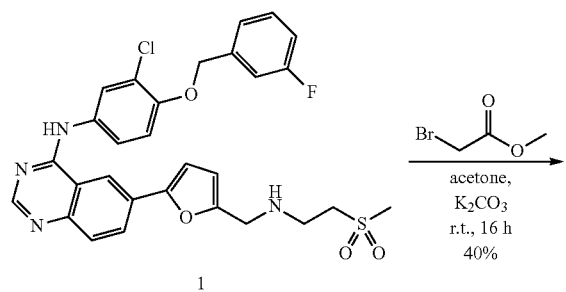

TABLE 3-1

Inhibition of ERBB2, EGFR, and CYP 3A4

[Structure: 4-[(3-chloro-4-(3-fluorobenzyloxy)phenyl)amino]-6-[5-((R-(2-methanesulfonylethyl)amino)methyl)furan-2-yl]quinazoline core]

| compound # | R | ERBB2 IC$_{50}$* | EGFR IC$_{50}$* | CYP3A4 IC$_{50}$** | Time-dep** CYP3A4 IC$_{50}$ | Ratio IC$_{50}$:TD*** |
|---|---|---|---|---|---|---|
| 1 | —H | + | + | + | + | + |
| 2 | —OH | − | + | − | − | ++ |
| 3 | H$_2$N-C(O)-O— | ++ | + | + | ++++ | ++ |
| 4 | Me$_2$N-C(O)-O— | − | − | +++ | ++++ | |
| 5 | MeO-C(O)-O— | +++ | +++ | − | − | ++ |
| 6 | HO$_2$C— | +++ | +++ | ++ | ++++ | +++ |
| 7 | MeO$_2$S— | +++ | ++ | +++ | ++++ | ++ |
| 8 | Ac— | + | ++ | − | ++++ | +++ |
| 9 | oxetan-3-yl | ++ | +++ | − | +++ | +++ |
| 10 | cyclobutyl | ++ | +++ | +++ | +++ | + |

*"+": IC$_{50}$ similar to lapatinib;
"−": IC$_{50}$ >25% greater than IC$_{50}$ of lapatinib;
"++": IC$_{50}$ >25% smaller than IC$_{50}$ of lapatinib;
"+++": IC$_{50}$ >50% smaller than IC$_{50}$ of lapatanib.

Example 4

Compound Cytotoxicity Against BT-474 & N87 Cell Lines

In this Example, experiments conducted to assess the cytotoxicity of lapatinib and compounds 5, 6, 7, 9, 10 (i.e., test compounds) are described. All of the test compounds were kept between 4° C. to 8° C. in solid form or as solution in DMSO.

The cell lines BT-474 and NCI-N87 were obtained from the ATCC. The cell lines were maintained in liquid nitrogen. Cell lines were prepared by thawing a 1 mL vial of the cell line and splitting it into two T-75 flasks with 10 mL of the appropriate media. BT-474 and NCI-N87 both utilized RPMI 1640 with varying glucose content (1 g/L for BT-474 and 4.5 g/L for NCI-N87). The cell lines were trypsinized and split into two T-150 flasks each time the cell lines reached 70-90% confluency.

When there were at least two confluent T-150 flasks of cell lines available, cultures were trypsinized and the cells enumerated using a hemocytometer and added to a 96-well microtiter plate at $1.5 \times 10^5$ cells/mL. The 96-well plates were then incubated at 37° C. with 5% $CO_2$ for 24 hours to allow enough time for the cells to adhere to the wells. After 24 hours, the media was aspirated and the cells were treated with each test compound starting at 0.1 mM with 2-fold dilutions thereafter. Lapatinib and media without the test compounds were used as controls. All 96-well plates were incubated at 37° C. with 5% $CO_2$ for 3 days with plates containing BT-474 and for 6 days with plates containing NCI-N87. After each incubation period, the treatments were aspirated and replaced with fresh media to allow the cells to recover for 24 hours. After recovery, cell viability was determined using the CellTiter 96® Aqueous One Solution Cell Proliferation Assay kit (Promega). The optical density (OD) was read using a SPECTRAMAX® M5 Microplate Reader (Molecular Devices) at 490 nm. The 50% inhibitory concentration ($IC_{50}$) was calculated by plotting OD versus log of the compound concentration (mM) in GraphPad Prism 4 (GraphPad) using the sigmoidal dose-response equation. All experiments were performed at least in duplicate.

Figure 2:
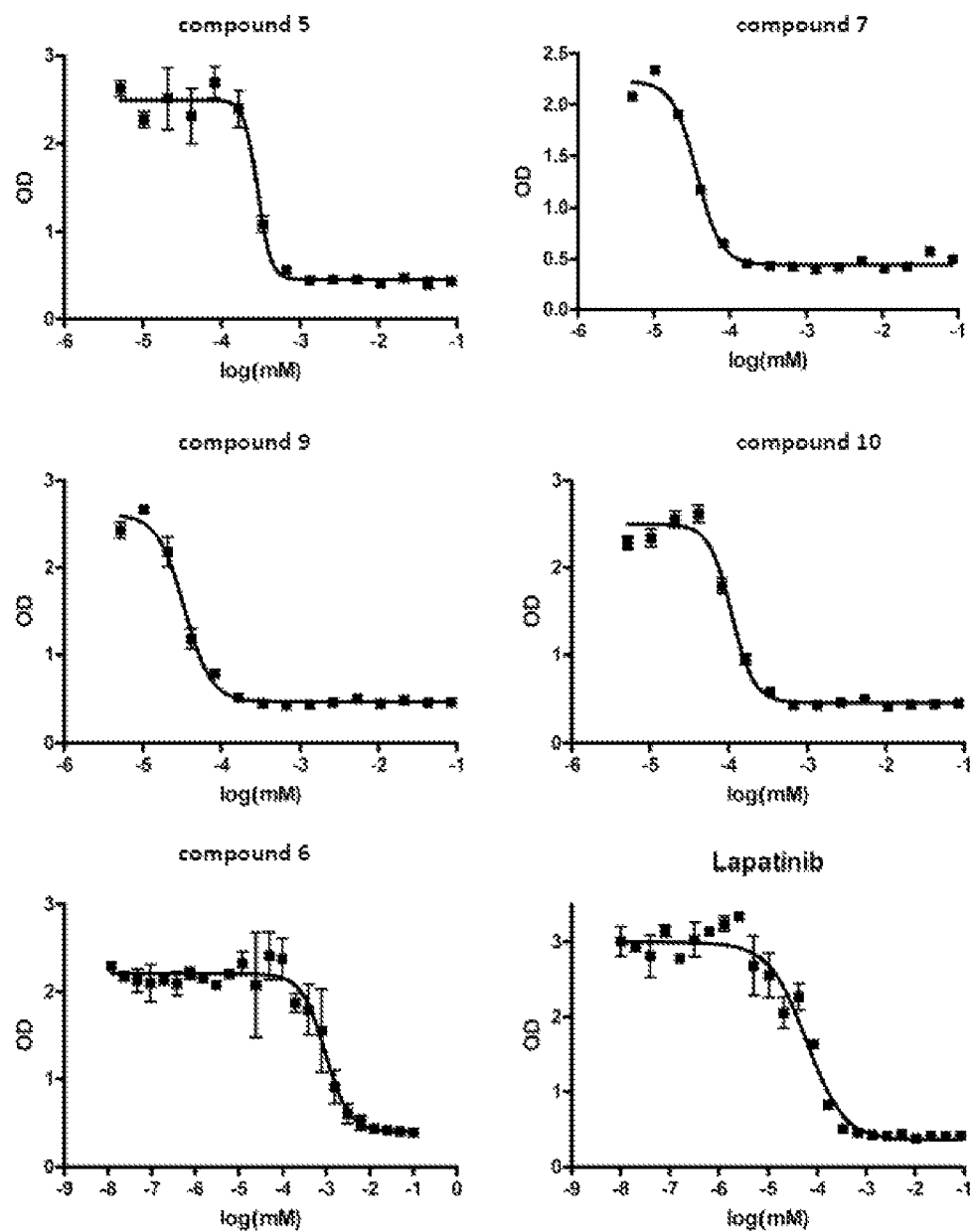
FIG. 2 provides graphs showing the cytotoxicity of various compounds tested in assays with NCI-N87 cells.

Summaries of the cytotoxicity data are provided in Table 4-1, and FIGS. 1 and 2. As indicated, two test compounds consistently provided a lower $IC_{50}$ than lapatinib, when tested against both BT-474 and NCI-N87, 83-034-P1 and 96-023-1.

TABLE 4-1

$IC_{50}$s Values

| Test Compound | BT-474 $IC_{50}$* | NCI-N87 $IC_{50}$* |
|---|---|---|
| Compound 5 | − | − |
| Compound 9 | ++ | ++ |
| Compound 6 | − | − |
| Compound 7 | ++ | ++ |
| Compound 10 | + | − |
| Lapatinib | + | + |

*"+": $IC_{50}$ similar to lapatinib; "−": $IC_{50}$ >25% greater than $IC_{50}$ of lapatinib; "++": $IC_{50}$ >25% smaller than $IC_{50}$ of lapatinib.

All of the test compounds had significant activity against the two cell lines, with compounds 7 and 9 showing $IC_{50}$ values lower than those observed for lapatinib.

Example 5

Synthesis and Biochemical Testing of Select Analogues

A subset of the lapatanib analogs prepared as described in Example 2 were tested for their inhibition of human EGFR and human ErbB2. The synthesis and biochemical testing of these compounds was completed using alternate CROs as a control for characterizing compounds.

Assay Protocols

Kinase assays were performed at RBC using standard protocols known to those skilled in the art. In brief, kinase, any required cofactors, substrate in DMSO, and kinase reaction mixture (by acoustic technology; Echo 550; nano-liter range) were incubated for 20 minutes at room temperature. 33P-ATP was added to initiate the reaction, which was incubated for 2 hours at room temperature. Kinase activity was detected by a standard filter-binding method.

Assay Results

As shown in Table 5-1, one of the four compounds tested (6) inhibited ErbB2 and EGFR with better potency than lapatinib.

TABLE 5-1

Inhibition of ERBB2 and EGFR

| Compound # | R | ErbB2 $IC_{50}$ | EGFR $IC_{50}$ |
|---|---|---|---|
| 1 | —H | + | + |
| 6 | $HO_2C$— | +++ | +++ |
| N/A | $MeO_2C$— | − | − |
| 7 | $MeO_2S$— | − | − |
| 9 | oxetanyl— | + | + |

* "+": $IC_{50}$ similar to lapatinib;
"−": $IC_{50}$ >25% greater than $IC_{50}$ of lapatinib;
"+++": $IC_{50}$ >50% smaller than $IC_{50}$ of lapatinib.

Example 6

Compound Cytotoxicity Against BT-474 Cell Lines

In this Example, experiments conducted at RBC to assess the cytotoxicity of lapatinib and compounds 1, 6, 7, 9, and 14 (i.e., test compounds) are described. All of the test compounds were kept between 4° C. to 8° C. in solid form or as solution in DMSO.

The cell line BT-474 was obtained from the ATCC. Test compounds were dissolved in DMSO (10 mM stock). Cell Titer-Glo® 2.0 Luminescent cell viability assay reagent was obtained from Promega. BT474 human breast cancer cell line was grown in Hybri-care medium supplemented with 1.5 g/L sodium bicarbonate and 10% FBS. 100 μg/ml penicillin and 100 μg/ml streptomycin were added to all culture media. Cultures were maintained at 37° C. in a humidified atmosphere of 5% $CO_2$ and 95% air. Test compounds in DMSO were added in a source plate. 25 nL of test compounds was delivered from the source plate to each well of the 384-well cell culture plates by Echo 550. 25 μl of culture medium containing 1000 cells for each cell line was added to the wells of the cell culture plates. Cells were incubated with test compounds at 37° C., 5% $CO_2$ for 72 hours. 25 μl of Cell Titer Glo 2.0 reagent was added to each well. The contents were mixed on an orbital shaker for 2 minutes and incubated at room temperature for 10 minutes to stabilize luminescent signal Luminescence was recorded by Envision 2104 Multilabel Reader (Perkin Elmer). The number of viable cells in culture was determined based on quantization of the ATP present in each culture well. The $IC_{50}$ values were calculated and the $IC_{50}$ curves were plotted using the GraphPad Prism 4 program based on a sigmoidal dose-response equation.

The cytotoxicity data are provided in Table 6-1. As indicated, two test compounds (9 and 14) provided a lower $IC_{50}$ than lapatinib, when tested against BT-474.

TABLE 6-1

$IC_{50}$ Values

| Test Compound | BT-474 $IC_{50}$ |
| --- | --- |
| Lapatinib | + |
| Compound 1 | − |
| Compound 6 | − |
| Compound 9 | ++ |
| Compound 14 | ++ |

* "+": $IC_{50}$ similar to lapatinib; "−": $IC_{50}$ >25% greater than $IC_{50}$ of lapatinib; "++": $IC_{50}$ >25% smaller than $IC_{50}$ of lapatinib.

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of the present invention.

We claim:

1. A method for producing an improved kinase inhibitor analog comprising exposing a starting kinase inhibitor to a cytochrome P450 monooxygenase to produce an analog, purifying said analog, and determining the kinase inhibition activity of said analog, wherein the kinase inhibition activity of said analog is determined against a kinase comprising EGFR, ErbB2, ErbB4, or Syk.

2. The method of claim 1, wherein said kinase inhibitor analog comprises an introduced hydroxyl moiety.

3. The method of claim 1, wherein said kinase inhibitor analog is further modified to provide additional kinase inhibitors.

4. The method of claim 2, wherein the site of hydroxylation is further modified chemically to provide new kinase inhibitors.

5. The method of claim 1, wherein the starting kinase inhibitor is lapatinib.

* * * * *